United States Patent
Echigo et al.

(10) Patent No.: US 10,377,734 B2
(45) Date of Patent: Aug. 13, 2019

(54) RESIST COMPOSITION, METHOD FOR FORMING RESIST PATTERN, POLYPHENOL DERIVATIVE FOR USE IN THE COMPOSITION

(71) Applicant: Mitsubishi Gas Chemical Company, Inc., Tokyo (JP)

(72) Inventors: Masatoshi Echigo, Kanagawa (JP); Masako Yamakawa, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 167 days.

(21) Appl. No.: 14/766,658

(22) PCT Filed: Jan. 28, 2014

(86) PCT No.: PCT/JP2014/051775
§ 371 (c)(1),
(2) Date: Aug. 7, 2015

(87) PCT Pub. No.: WO2014/123032
PCT Pub. Date: Aug. 14, 2014

(65) Prior Publication Data
US 2015/0376157 A1    Dec. 31, 2015

(30) Foreign Application Priority Data

Feb. 8, 2013   (JP) .................. 2013-023641

(51) Int. Cl.
| | |
|---|---|
| G03F 7/004 | (2006.01) |
| G03F 7/32 | (2006.01) |
| C07D 311/78 | (2006.01) |
| C07C 69/017 | (2006.01) |
| C07C 69/96 | (2006.01) |
| C07C 69/734 | (2006.01) |
| G03F 7/039 | (2006.01) |
| G03F 7/16 | (2006.01) |
| G03F 7/20 | (2006.01) |

(52) U.S. Cl.
CPC .......... *C07D 311/78* (2013.01); *C07C 69/017* (2013.01); *C07C 69/734* (2013.01); *C07C 69/96* (2013.01); *G03F 7/0045* (2013.01); *G03F 7/0392* (2013.01); *G03F 7/16* (2013.01); *G03F 7/20* (2013.01); *G03F 7/32* (2013.01); *C07C 2601/14* (2017.05)

(58) Field of Classification Search
CPC ............ G03F 7/0392; G03F 7/30; G03F 7/32; G03F 7/0045; C07D 311/00; C07D 311/78
USPC ................ 430/270.1, 326; 549/382
See application file for complete search history.

(56) References Cited

U.S. PATENT DOCUMENTS

| | | | | |
|---|---|---|---|---|
| 2,100,798 | A |  | 11/1937 | Dilthey et al. |
| 2,546,872 | A |  | 3/1951 | Schmid et al. |
| 3,947,468 | A |  | 3/1976 | Hall et al. |
| 4,252,884 | A | * | 2/1981 | Bennett ............... G03C 1/58 430/147 |
| 4,289,839 | A | * | 9/1981 | DiPippo ............... G03C 1/54 430/147 |
| 4,482,489 | A | * | 11/1984 | DiPippo ............... G03C 1/56 430/136 |
| 4,579,758 | A |  | 4/1986 | Dorsch et al. |
| 5,332,648 | A |  | 7/1994 | Kihara et al. |
| 5,986,094 | A |  | 11/1999 | Ghoshal |

(Continued)

FOREIGN PATENT DOCUMENTS

| | | |
|---|---|---|
| CN | 1414031 | 4/2003 |
| CN | 1853141 A | 10/2006 |

(Continued)

OTHER PUBLICATIONS

International Search Report dated Feb. 25, 2014 for PCT/JP2012/051775 and English translation of the same (4 pages).

(Continued)

*Primary Examiner* — John S Chu
(74) *Attorney, Agent, or Firm* — Fitch, Even, Tabin & Flannery LLP

(57) ABSTRACT

The present invention provides a resist composition which is excellent in heat resistance, has high solubility in a safe solvent, has high sensitivity, and can impart a good shape to a resist pattern. Such a resist composition contains a compound represented by the following general formula (1) or (2):

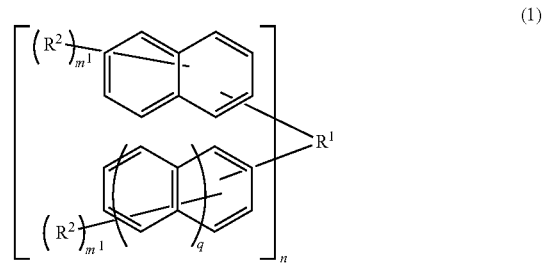

(1)

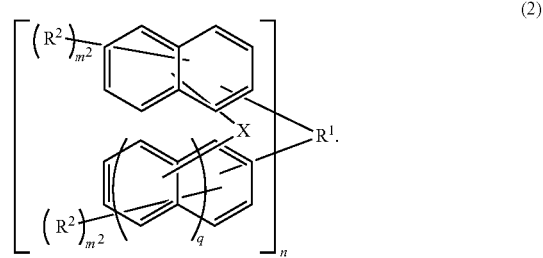

(2)

19 Claims, No Drawings

(56) References Cited

U.S. PATENT DOCUMENTS

| | | | | |
|---|---|---|---|---|
| 6,784,228 B2 * | 8/2004 | Ogura | | C07D 311/78 |
| | | | | 523/466 |
| 6,794,408 B2 | 9/2004 | Eder | | |
| 7,871,751 B2 * | 1/2011 | Echigo | | G03F 7/0382 |
| | | | | 430/270.1 |
| 9,136,121 B2 | 9/2015 | Hatakeyama | | |
| 9,274,426 B2 | 3/2016 | Rahman | | |
| 9,316,913 B2 * | 4/2016 | Echigo | | G03F 7/091 |
| 9,540,339 B2 | 1/2017 | Echigo | | |
| 9,908,831 B2 | 3/2018 | Echigo | | |
| 2002/0106909 A1 | 8/2002 | Kato et al. | | |
| 2003/0092852 A1 | 5/2003 | Ogura et al. | | |
| 2004/0197709 A1 | 10/2004 | Arase et al. | | |
| 2005/0074695 A1 | 4/2005 | Nakamura | | |
| 2005/0255712 A1 | 11/2005 | Kato et al. | | |
| 2007/0059632 A1 | 3/2007 | Oguro et al. | | |
| 2007/0172759 A1 | 7/2007 | Ogihara et al. | | |
| 2007/0232839 A1 | 10/2007 | Yoshitomo | | |
| 2007/0275325 A1 | 11/2007 | Hatakeyama | | |
| 2008/0113294 A1 | 5/2008 | Echigo | | |
| 2008/0138744 A1 | 6/2008 | Hatanaka et al. | | |
| 2008/0153031 A1 * | 6/2008 | Echigo | | G03F 7/0382 |
| | | | | 430/281.1 |
| 2009/0171061 A1 | 7/2009 | Sue et al. | | |
| 2009/0261300 A1 | 10/2009 | Watanabe | | |
| 2010/0047709 A1 | 2/2010 | Echigo | | |
| 2010/0099044 A1 | 4/2010 | Hatakeyama | | |
| 2010/0104977 A1 | 4/2010 | Hatakeyama | | |
| 2010/0136477 A1 * | 6/2010 | Ng | | G03F 7/0045 |
| | | | | 430/270.1 |
| 2010/0207516 A1 | 8/2010 | Moriwaki et al. | | |
| 2010/0227859 A1 | 9/2010 | Li | | |
| 2010/0285407 A1 | 11/2010 | Ogihara | | |
| 2010/0316950 A1 | 12/2010 | Oguro et al. | | |
| 2011/0177459 A1 | 7/2011 | Ogihara et al. | | |
| 2011/0311920 A1 | 12/2011 | Kinsho et al. | | |
| 2012/0064725 A1 | 3/2012 | Kinsho et al. | | |
| 2012/0171611 A1 | 7/2012 | Ideno et al. | | |
| 2012/0184103 A1 | 7/2012 | Ogihara et al. | | |
| 2012/0220112 A1 | 8/2012 | Hatakeyama | | |
| 2012/0228584 A1 | 9/2012 | Wigglesworth et al. | | |
| 2013/0056653 A1 | 3/2013 | Hatakeyama et al. | | |
| 2013/0087529 A1 | 4/2013 | Hatakeyama | | |
| 2013/0150627 A1 * | 6/2013 | Okada | | C07C 37/72 |
| | | | | 568/719 |
| 2014/0186776 A1 | 7/2014 | Uchiyama et al. | | |
| 2014/0248556 A1 | 9/2014 | Kato | | |
| 2014/0248561 A1 * | 9/2014 | Echigo | | C07D 311/96 |
| | | | | 430/281.1 |
| 2014/0308615 A1 | 10/2014 | Echigo | | |
| 2014/0319097 A1 | 10/2014 | Kim et al. | | |
| 2014/0363957 A1 | 12/2014 | Hatakeyama | | |
| 2014/0363958 A1 | 12/2014 | Hatakeyama | | |
| 2015/0090691 A1 | 4/2015 | Echigo et al. | | |
| 2015/0309403 A1 | 10/2015 | Rahman | | |
| 2015/0368224 A1 * | 12/2015 | Echigo | | C07C 41/01 |
| | | | | 549/382 |
| 2015/0376157 A1 | 12/2015 | Echigo et al. | | |
| 2015/0376158 A1 | 12/2015 | Echigo et al. | | |
| 2015/0376202 A1 | 12/2015 | Echigo et al. | | |
| 2016/0130243 A1 | 5/2016 | Satou | | |
| 2016/0145231 A1 * | 5/2016 | Echigo | | C07D 311/96 |
| | | | | 430/270.1 |
| 2017/0183279 A1 | 6/2017 | Echigo | | |
| 2017/0349564 A1 | 12/2017 | Toida | | |

FOREIGN PATENT DOCUMENTS

| | | |
|---|---|---|
| CN | 102070595 | 5/2011 |
| CN | 103733136 A | 4/2014 |
| EP | 1275673 | 1/2003 |
| EP | 1 300 403 A | 4/2003 |
| EP | 1666970 | 6/2006 |
| EP | 2 743 769 A1 | 6/2014 |
| EP | 2743249 | 6/2014 |
| EP | 2743770 A1 | 6/2014 |
| JP | S48049508 A | 7/1973 |
| JP | 62094841 A | 5/1987 |
| JP | H01-283280 A | 11/1989 |
| JP | H04217675 | 8/1992 |
| JP | H05034913 A | 2/1993 |
| JP | H05-134415 A | 5/1993 |
| JP | H05163290 A | 6/1993 |
| JP | 05216235 A | 8/1993 |
| JP | H06-049402 A | 2/1994 |
| JP | H06-242607 A | 9/1994 |
| JP | H07-215833 A | 8/1995 |
| JP | H10-25220 A | 1/1998 |
| JP | H10045764 A | 2/1998 |
| JP | H11-072925 A | 3/1999 |
| JP | 2001042525 | 2/2001 |
| JP | 2002-214769 A | 7/2002 |
| JP | 2002-334869 A | 11/2002 |
| JP | 2002-334896 A | 11/2002 |
| JP | 2002-341542 A | 11/2002 |
| JP | 2003-201333 A | 7/2003 |
| JP | 2004177668 A | 6/2004 |
| JP | 2004271838 A | 9/2004 |
| JP | 2005-250434 A | 9/2005 |
| JP | 2005-326838 A | 11/2005 |
| JP | 2005326868 A | 11/2005 |
| JP | 2005-346024 A | 12/2005 |
| JP | 2006-036648 A | 2/2006 |
| JP | 2006098869 | 4/2006 |
| JP | 2006113136 | 4/2006 |
| JP | 2006160663 | 6/2006 |
| JP | 2006-213634 A | 8/2006 |
| JP | 2006259482 A | 9/2006 |
| JP | 2007-019294 A | 1/2007 |
| JP | 2007-199653 A | 8/2007 |
| JP | 2007-226170 A | 9/2007 |
| JP | 2007-226203 A | 9/2007 |
| JP | 2007-262398 A | 10/2007 |
| JP | 2007-326847 A | 12/2007 |
| JP | 2008-065081 A | 3/2008 |
| JP | 2008-145539 A | 6/2008 |
| JP | 2008201954 A | 9/2008 |
| JP | 2008-239868 A | 10/2008 |
| JP | 2009-073738 A | 4/2009 |
| JP | 2009-098155 A | 5/2009 |
| JP | 2009-108313 A | 5/2009 |
| JP | 2009-155256 A | 7/2009 |
| JP | 2009-173623 A | 8/2009 |
| JP | 2009300978 | 12/2009 |
| JP | 2010160189 | 7/2010 |
| JP | 2010-170013 A | 8/2010 |
| JP | 2010-219295 A | 9/2010 |
| JP | 2010235643 | 10/2010 |
| JP | 2011-068624 A | 4/2011 |
| JP | 2011-105887 A | 6/2011 |
| JP | 2011-150023 A | 8/2011 |
| JP | 2012-1687 A | 1/2012 |
| JP | 2012068652 | 4/2012 |
| JP | 2012-145897 A | 8/2012 |
| JP | 2013-064978 A | 4/2013 |
| JP | 2013-087173 A | 5/2013 |
| JP | 2013083833 | 5/2013 |
| JP | 2013137524 A | 7/2013 |
| JP | 2013253161 A | 12/2013 |
| JP | 2014196288 A | 10/2014 |
| JP | 2014205746 | 10/2014 |
| KR | 10-2010-0095563 A | 8/2010 |
| WO | 9736960 | 10/1997 |
| WO | 02/14434 A1 | 2/2002 |
| WO | 03/017002 A1 | 2/2003 |
| WO | 2004-066377 A1 | 8/2004 |
| WO | 2005029189 A1 | 3/2005 |
| WO | 2005/111724 A1 | 11/2005 |
| WO | 2006068267 A1 | 6/2006 |
| WO | 2007/097457 A1 | 8/2007 |
| WO | 2008053974 A1 | 5/2008 |
| WO | 2008137816 A2 | 11/2008 |
| WO | 2009-072465 A1 | 6/2009 |

(56) References Cited

FOREIGN PATENT DOCUMENTS

| WO | 2009/119201 A1 | 10/2009 |
|---|---|---|
| WO | 2009119201 A1 | 10/2009 |
| WO | 2009/145224 A1 | 12/2009 |
| WO | 2011-034062 A1 | 3/2011 |
| WO | 2012-165507 A1 | 12/2012 |
| WO | 2013/024779 A1 | 2/2013 |
| WO | 2013024777 A1 | 2/2013 |
| WO | 2013/066067 A1 | 5/2013 |
| WO | 2013184755 | 12/2013 |
| WO | 2014050690 | 4/2014 |
| WO | 2014123032 A1 | 8/2014 |
| WO | 2014199660 | 12/2014 |

OTHER PUBLICATIONS

T. Nakayama, M. Nomura, K. Haga, M. Ueda, Bull. Chem. Soc. Jpn., 71, 2979 (1998).
Shinji Okazaki et al., Innovation of Photoresist Material Development, CMC Publishing Co., Ltd., Sep. 2009, p. 211-259 (No English translation available).
English Translation of JP H01-283280 A, Nov. 14, 1989.
Machine English Translation of JP 2008-239868 A, Oct. 9, 2008.
International Search Report dated Sep. 11, 2012 for International Application No. PCT/JP2012/070305 with English Translation (5 pages).
International Search Report dated Mar. 25, 2014 for International Application No. PCT/JP2014/052524 with English Translation (8 pages).
International Search Report dated May 13, 2014 for International Application No. PCT/JP2014/052530 with English Translation (8 pages).
Nishiyama Tomihiro et al., Antioxidant activities of fused heterocyclic compounds, xanthene-2,7-diols with BHT or catechol skeleton, Polymer Degradation and Stability, 1998, vol. 62, No. 3, pp. 529-534.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,f]thiepin, Part CXXXIII in the series Neurotropic and Psychotropic Agents, Collection of Czechoslovak Chemical Communications, 1979, vol. 44, No. 10, pp. 2987-2996.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[f]chroman, Journal of Heterocyclic Chemistry, Mar. 1, 1998, vol. 35, No. 2, pp. 457-460.
Jha Amitabh and Beal Jennifer, "Convenient synthesis of 12H-benzo[a]xanthenes from 2-tetralone," Tetrahedron Letters, 2004, vol. 45, No. 49, pp. 8999-9001.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Ghodratbeigi Mohsen et al., "Design, modeling and synthesis of molecular tweezers with self-assembly properties," Journal of Molecular Structure, 2011, vol. 990, No. 1, pp. 140-151.
Hagihara K. et al., "The effect of Ti-addition on plastic deformation and fracture behavior of directionally solidified NiAl/Cr(Mo) eutetic alloys," Intermetallics, 2006, vol. 14, No. 10, pp. 1326-1331.
Osman A-M, Reactions Between Chloro-p-benzoquinones and Beta-Naphtol, Journal of Organic Chemistry, 1957, vol. 22, pp. 342-344.
Ahmed Munir et al., The Direct Bradsher Reaction. Part I. Synthesis of Thiophen Analogues of Linear Polycyclic Hydrocarbons, Journal of the Chemical Society, Perkin Transactions I, 1973, pp. 1099-1103.
Sirringhaus Henning et al., Dibenzothienobisbenzothiophene—a novel fused-ring oligomer with high field-effect mobility, Journal of Materials Chemistry, 1999, vol. 9, pp. 2095-2101.
Written Opinion of the International Searching Authority issued in International Application No. PCT/JP2012/070304 (including translation), dated Oct. 23, 2012.
Brecher, Jonathan, Graphical Representation Standards for Chemical Structure Diagrams, Pure Appl. Chem., 2008, pp. 277-410, vol. 80, No. 2, Cambridge, Massachusetts.
Journal of the Chemical Society, p. 5336-5341 (Nov. 1963).
Nature, 161:930-931 (1948).
International Search Report dated Oct. 23, 2012 issued in International Application No. PCT/JP2012/070304.
Ohishi Takeshi. Tetrahedron Letters 42 (2001) 2493-2496.
Clowes, G. A., et al., "Studies of the Scholl reaction: Oxidative Dehydrogenation involving 1-Ethoxynaphthylenen and Related Compounds," J Chem. Soc (C) 2519-2526 (1968).
Cameron, Donald W., et al., "Synthesis of a natural polychloro dinaphthofuran quinone," Tetrahedron Letters, 1980, vol. 21(14), pp. 1385-1386.
Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.
Areephong, Jetsuda, et al., "A concise synthesis of functionalized 7-oxa-[5]-helicenes," Tetrahedron Letters, 2004, vol. 45, pp. 3067-3070.
Protiva, Miroslav, et al., "Potential metabolites or tricyclic neuroleptics" 3,7-dimethoxy and 7,8-dimethoxy derivatives of 10-{4-methylpiperazino )-10,11-dihydrodibenzo[b,f]thiepin, Collection of Czechoslovak Chemical Communications, 1981, vol. 46, pp. 1808-1817.
Bentley, K. W., and Robinson, R., "A Synthesis of alpha-Anhydrotrimethylbrazilone," Tetrahedron Letters, 1959, vol. 1, Issue 2, pp. 11-14.
Dann, von Otto, and Hofmann, Hans, Synthese von ()-Brasilin, Justus Liebigs Annalen der Chemie, 1963, vol. 667, Issue 1, pp. 116-125.
Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305.
International Search Report dated Feb. 9, 2016, for PCT/JP2015/084907 and English translation of the same (7 pages).
International Search Report on Patentability for PCT/JP2016/056332 dated May 31, 2016; English translation submitted herewith (11 pages).
Tian- jun Liu, Ke-shen Zhang, Yong-jun Chen, Dong Wang and Chao-jun Li, "Chiral Conjugated Oligomer Based on 1, 1'-Binol With 3, 3 ' -Acetylene -Phenylene-Acetylene Spacer", Chinese Journal of Polymer Science, Mar. 8, 2001, vol. 19, No. 5, p. 521-526.
International Search Report on Patentability for PCT/JP2016/056333 dated May 24, 2016; English translation submitted herewith (7 pages).
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.
European Journal of Medicinal Chemistry, published bi-monthly, Ejmcs, 13(4): 381-385 (1978).
Skandinavisches Archiv fuer Physiologie, 43: 215-243 (1923).
International Preliminary Report on Patentability issued in International Application No. PCT/JP2012/070304.
Shinji Okazaki et al., "New Trends of Photoresists", CMC Publishing Co., Ltd., Sep. 2009, p. 211-259.

(56) References Cited

OTHER PUBLICATIONS

International Search Report for PCT/JP2014/051775 dated Feb. 25, 2014 and English translation (4 pages).

\* cited by examiner

RESIST COMPOSITION, METHOD FOR FORMING RESIST PATTERN, POLYPHENOL DERIVATIVE FOR USE IN THE COMPOSITION

CROSS-REFERENCE TO RELATED APPLICATIONS

This application is a U.S. national phase application filed under 35 U.S.C. § 371 of International Application PCT/JP2014/051775, filed on Jan. 28, 2014, designating the United States, which claims priority from Japanese Application Number 2013-023641, filed Feb. 8, 2013, which are hereby incorporated herein by reference in their entirety.

TECHNICAL FIELD

The present invention relates to a resist composition and a method for forming a resist pattern using the composition.

The present invention also relates to a polyphenol derivative that can be used in the above resist composition, etc.

BACKGROUND ART

Conventionally known typical resist materials are polymer based materials capable of forming amorphous thin films. For example, a line pattern of about 45 to 100 nm is formed by coating a substrate with a solution of a polymer resist material such as polymethyl methacrylate, polyhydroxy styrene with an acid dissociation reactive group, or polyalkyl methacrylate to prepare a resist thin film and then irradiating the resist thin film with ultraviolet, far ultraviolet, electron beam, extreme ultraviolet (EUV), and X-ray or the like.

However, polymer based resists have a molecular weight as large as about 10,000 to 100,000 and also wide molecular weight distribution. Therefore, in lithography using a polymer based resist, roughness occurs on a fine pattern surface; the pattern dimension becomes difficult to be controlled; and the yield is decreased. Therefore, there is a limitation in miniaturization with lithography using a conventional polymer based resist material. Then, in order to make a finer pattern, various low molecular weight resist materials have been proposed.

For example, an alkaline development type negative type radiation-sensitive composition (see Japanese Patent Application Laid-Open No. 2005-326838 and Japanese Patent Application Laid-Open No. 2008-145539) using a low molecular weight polynuclear polyphenol compound as a main component has been suggested. Additionally, as a candidate of a low molecular weight resist material having high heat resistance, an alkaline development type negative type radiation-sensitive composition (see Japanese Patent Application Laid-Open No. 2009-173623 and T. Nakayama, M. Nomura, K. Haga, M. Ueda: Bull. Chem. Soc. Jpn., 71, 2979 (1998)) using a low molecular weight cyclic polyphenol compound as a main component has also been suggested.

As a base compound of a resist material, a polyphenol compound is known to be useful in imparting high heat resistance and improving the resolution or roughness of a resist pattern, in spite of its low molecular weight (see Shinji Okazaki et al., "Innovation of Photoresist Material Development", CMC Publishing Co., Ltd., September 2009, p. 211-259).

SUMMARY OF INVENTION

However, the compositions described in Japanese Patent Application Laid-Open No. 2005-326838 and Japanese Patent Application Laid-Open No. 2008-145539 have the disadvantages that the heat resistance is not sufficient and the shape of the resulting resist pattern becomes poor. The compositions described in Japanese Patent Application Laid-Open No. 2009-173623 and T. Nakayama, M. Nomura, K. Haga, M. Ueda: Bull. Chem. Soc. Jpn., 71, 2979 (1998) have problems such as low solubility in a safe solvent used in a semiconductor production process, low sensitivity, and the poor shape of the resulting resist pattern. Therefore, further improvement in such low molecular weight resist materials is desired.

Shinji Okazaki et al., "Innovation of Photoresist Material Development", CMC Publishing Co., Ltd., September 2009, p. 211-259 makes no mention about solubility. Still, the heat resistance of the compounds described therein is not sufficient. Further improvement is desired in terms of characteristics such as heat resistance, water resistance, chemical resistance, electrical characteristics, and mechanical characteristics.

An object of the present invention is to provide a resist composition which is excellent in heat resistance, has high solubility in a safe solvent, has high sensitivity, and can impart a good shape to a resist pattern, and a method for forming a resist pattern using the resist composition.

Another object of the present invention is to provide a polyphenol derivative which is excellent in heat resistance and has high solubility in a safe solvent.

The inventors have, as a result of intensive studies to solve the above problems, found out that by containing a compound having a specific structure, a resist composition is excellent in heat resistance, has high solubility in a safe solvent, has high sensitivity, and can impart a good shape to a resist pattern, and reached the present invention.

More specifically, the present invention is as follows.

[1]

A resist composition comprising a compound represented by the following formula (1) or (2):

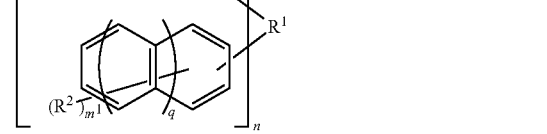

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^2$ is independently a hydrogen atom, a halogen atom, a linear, branched, or cyclic alkyl group of 1 to 10 carbon atoms, an aryl group of 6 to 10 carbon atoms, an alkenyl group of 2 to 10 carbon atoms, a hydroxyl group, or a group in which a hydrogen atom of a hydroxyl group is substituted with an acid dissociation group, and may be the same as or different from each other on the same naphthalene ring or benzene ring; at least one of $R^2$ is a group in which a hydrogen atom of a hydroxyl group is substituted with an acid dissociation group; n is an integer of 1 to 4; structural formulas of repeating units in the formulas (1) and (2) may be the same as or different from each other; in the formula (1), each $m^1$ is independently an integer of 1 to 7; and in the formula (2), each X is independently an oxygen atom or a sulfur atom, each $m^2$ is independently an integer of 1 to 6, and each q is independently 0 or 1.

[2]

The resist composition according to the above [1], wherein the compound represented by the formula (1) is a compound represented by the following formula (1-1), and the compound represented by the formula (2) is a compound represented by the following formula (2-1):

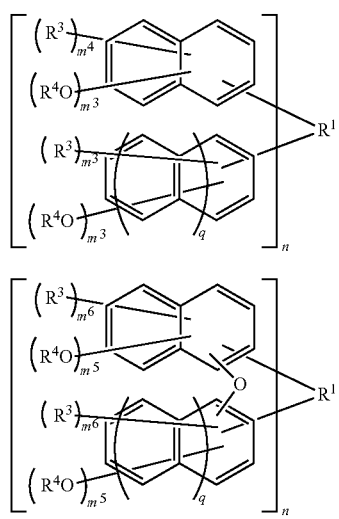

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^3$ is independently a hydrogen atom, a linear, branched, or cyclic alkyl group of 1 to 10 carbon atoms, an aryl group of 6 to 10 carbon atoms, or an alkenyl group of 2 to 10 carbon atoms and may be the same as or different from each other on the same naphthalene ring or benzene ring; each $R^4$ is independently a hydrogen atom or an acid dissociation group; at least one of $R^4$ is an acid dissociation group; structural formulas of repeating units in the formulas (1-1) and (2-1) may be the same as or different from each other; n is an integer of 1 to 4; in the formula (1-1), each $m^3$ is independently an integer of 1 to 7, each $m^4$ is independently an integer of 0 to 6, and each $m^3+m^4$ is independently an integer of 1 to 7; and in the formula (2-1), each $m^5$ is independently an integer of 1 to 6, each $m^6$ is independently an integer of 0 to 5, each $m^5+m^6$ is independently an integer of 1 to 6, and each q is independently 0 or 1.

[3]

The resist composition according to the above [1], wherein the compound represented by the formula (1) is a compound represented by the following formula (1-2), and the compound represented by the formula (2) is a compound represented by the following formula (2-2):

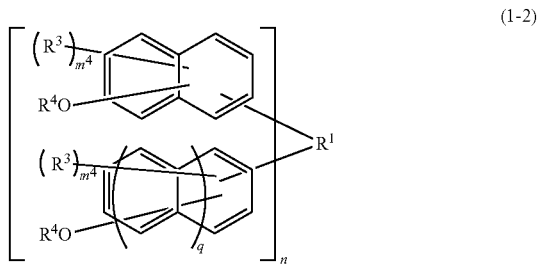

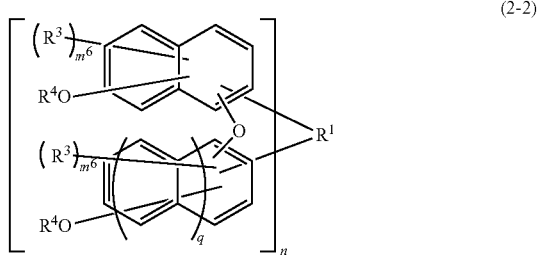

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^3$ is independently a hydrogen atom, a linear, branched, or cyclic alkyl group of 1 to 10 carbon atoms, an aryl group of 6 to 10 carbon atoms, or an alkenyl group of 2 to 10 carbon atoms and may be the same as or different from each other on the same naphthalene ring or benzene ring; each $R^4$ is independently a hydrogen atom or an acid dissociation group; at least one of $R^4$ is an acid dissociation group; structural formulas of repeating units in the formulas (1-2) and (2-2) may be the same as or different from each other; n is an integer of 1 to 4; in the formula (1-2), each $m^4$ is independently an integer of 0 to 6; and in the formula (2-2), each $m^6$ is independently an integer of 0 to 5, and each q is independently 0 or 1.

[4]

The resist composition according to the above [1], wherein the compound represented by the formula (1) is a compound represented by the following formula (3), and the compound represented by the formula (2) is a compound represented by the following formula (4):

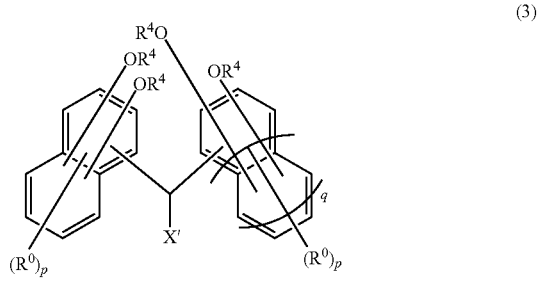

(4)

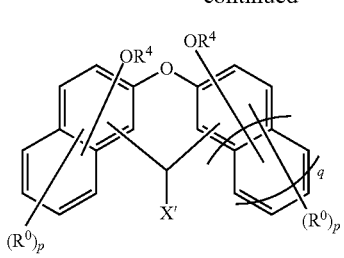

wherein X' is a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; each $R^4$ is independently a hydrogen atom or an acid dissociation group; at least one of $R^4$ is an acid dissociation group; each p is independently an integer of 0 to 5; and q is 0 or 1.

[5] The resist composition according to any one of the above items [1] to [4], further comprising a solvent.

[6] The resist composition according to any one of the above items [1] to [5], further comprising an acid generating agent.

[7]
The resist composition according to any one of the above [1] to [6], further comprising an acid diffusion controlling agent.

[8]
A method for forming a resist pattern, comprising the steps of:
coating a substrate with the resist composition according to any one of the above [1] to [7], thereby forming a resist film;
exposing the formed resist film; and
developing the exposed resist film.

The inventor has also, as a result of devoted examinations to solve the above problems, found out that the problems can be solved by means of a novel polyphenol derivative having a specific structure, and reached the present invention.

More specifically, the present invention is as follows.
[9]
A polyphenol derivative represented by the following formula (3) or (4):

(3)

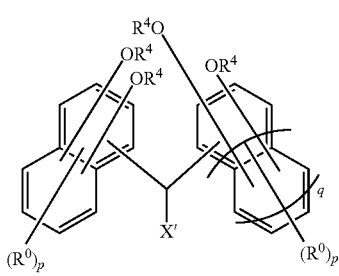

(4)

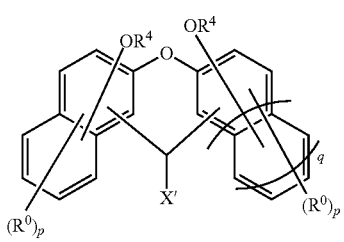

wherein X' is a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; each $R^4$ is independently a hydrogen atom or an acid dissociation group; at least one of $R^4$ is an acid dissociation group; each p is independently an integer of 0 to 5; and q is 0 or 1.

The present invention can provide a resist composition which is excellent in heat resistance, has high solubility in a safe solvent, has high sensitivity, and can impart a good shape to a resist pattern, and a method for forming a resist pattern using the resist composition.

The present invention can also provide a polyphenol derivative which is excellent in heat resistance and has high solubility in a safe solvent.

DESCRIPTION OF EMBODIMENTS

Hereinafter, an embodiment of the present invention will be described (hereinafter, referred to as "present embodiment"). The present embodiment is given in order to illustrate the present invention. The present invention is not limited to only the present embodiment. Various changes and modifications may be made in the present invention without departing from the sprit thereof.

[Resist Composition]

The resist composition of the present embodiment contains a compound represented by the above formula (1) or (2).

(Composition of First Aspect)

According to the first aspect, the resist composition of the present embodiment contains a compound represented by the following formula (1):

(1)

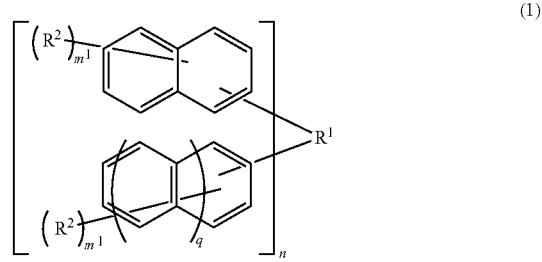

The chemical structure of the compound of the present embodiment can be determined by $^1$H-NMR analysis.

The composition of the present embodiment is excellent in heat resistance, mainly because the compound represented by the above formula (1) has a naphthalene skeleton.

In the formula (1), $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^2$ is independently a hydrogen atom, a halogen atom, a linear, branched, or cyclic alkyl group of 1 to 10 carbon atoms, an aryl group of 6 to 10 carbon atoms, an alkenyl group of 2 to 10 carbon atoms, a hydroxyl group, or a group in which a hydrogen atom of a hydroxyl group is substituted with an acid dissociation group, and may be the same as or different from each other on the same naphthalene ring or benzene ring; at least one of $R^2$ is a group in which a hydrogen atom of a hydroxyl group is substituted with an acid dissociation group; and each q is independently 0 or 1. The structural formulas of the repeating units may be the same or different from each other, each $m^1$ is independently an integer of 1 to 7, and n is an integer of 1 to 4. In terms of resist characteristics such as heat resistance, resolution, and roughness, n is preferably 1 to 3.

Also, q is preferably 1. That is, the compound represented by the above formula (1) is preferably represented by the following formula (1-a).

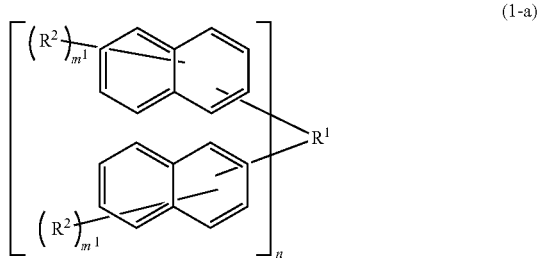

(1-a)

In the formula (1-a), $R^1$, $R^2$, $m^1$, and n are as defined in the above formula (1).

Although the compound of the present embodiment is not a polymer, the structure of the moiety [ ] bonded to $R^1$ in the above formula (1) is referred to as "the structural formula of a repeating unit" (hereinafter, the same holds true for the formula (2)) for the sake of convenience.

In the above formula (1), $R^1$ is a single bond or a 2n-valent hydrocarbon group of 1 to 30 carbon atoms (hereinafter, "of k to l carbon atoms" (k and l are integers) may be referred to as "Ck-l") wherein the hydrocarbon group may have a cyclic hydrocarbon group, a double bond, a heteroatom, or a C6-30 aromatic group.

The above 2n-valent hydrocarbon group refers to a C1-30 alkylene group (n=1), a C1-30 alkanetetrayl group (n=2), a C2-30 alkanehexayl group (n=3), or a C3-30 alkaneoctayl group (n=4). Examples of the above 2n-valent hydrocarbon group include ones having a linear, branched or cyclic structure.

The above 2n-valent hydrocarbon group may have a cyclic hydrocarbon group (except for an aromatic group), a double bond, a heteroatom (e.g., an oxygen atom, a nitrogen atom, and a sulfur atom), or a C6-30 aromatic group (e.g., groups having a benzene ring, a naphthalene ring, or an anthracene ring). Herein, the cyclic hydrocarbon group also includes bridged cyclic hydrocarbon groups. Specific examples thereof include groups having an adamantane ring, groups having a norbornene ring, and groups having a tricyclodecane structure.

$R^1$ preferably has a condensed polycyclic aromatic group (particularly, a bicyclic to tetracyclic condensed ring structure) in terms of heat resistance and preferably has a polyphenyl group such as a biphenyl group in terms of solubility in a safe solvent and heat resistance.

each $R^2$ is independently a hydrogen atom, a halogen atom, a C1-10 linear, branched, or cyclic alkyl group, a C6-10 aryl group, a C2-10 alkenyl group, a hydroxyl group, or a group in which a hydrogen atom of a hydroxyl group is substituted with an acid dissociation group, and may be the same as or different from each other on the same naphthalene ring or benzene ring; at least one of $R^2$ is a group in which a hydrogen atom of a hydroxyl group is substituted with an acid dissociation group; each $m^1$ is independently an integer of 1 to 7.

In terms of prevention of equipment contamination upon resist film exposure, $R^2$ is preferably a hydrogen atom, a C1-10 linear, branched, or cyclic alkyl group, a C6-10 aryl group, a C2-10 alkenyl group, or a hydroxyl group.

By virtue of the above structural features, the compound represented by the above formula (1) has high heat resistance due to its rigidity, in spite of its low molecular weight, and may be used even under high temperature baking conditions. Since the compound represented by the formula (1) has a low molecular weight and may be baked at a high temperature, the compound is highly sensitive and, in addition, can impart a good shape to a resist pattern.

In the present embodiment, in terms of solubility in a safe solvent and resist pattern characteristics, the compound represented by the above formula (1) is preferably a compound represented by the following formula (1-1).

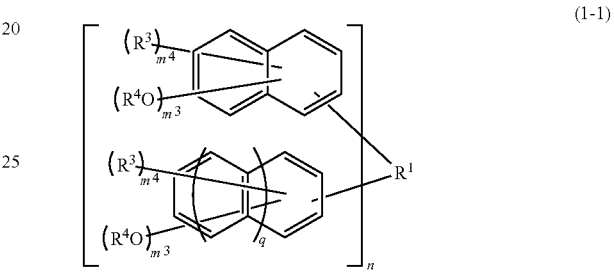

(1-1)

In the formula (1-1), $R^1$ is as defined in the above formula (1); each $R^3$ is independently a hydrogen atom, a C1-10 linear, branched, or cyclic alkyl group, a C6-10 aryl group, or a C2-10 alkenyl group and may be the same as or different from each other on the same naphthalene ring or benzene ring; each $R^4$ is independently a hydrogen atom or an acid dissociation group; at least one of $R^4$ is an acid dissociation group; the structural formulas of the repeating units in the formulas (1-1) and (2-1) may be the same as or different from each other; each $m^3$ is independently an integer of 1 to 7; each $m^4$ is independently an integer of 0 to 6; each $m^3+m^4$ is independently an integer of 1 to 7; and n is an integer of 1 to 4; each q is independently 0 or 1 and are preferably 1. That is, the compound represented by the above formula (1-1) is preferably a compound represented by the following formula (1-1-a).

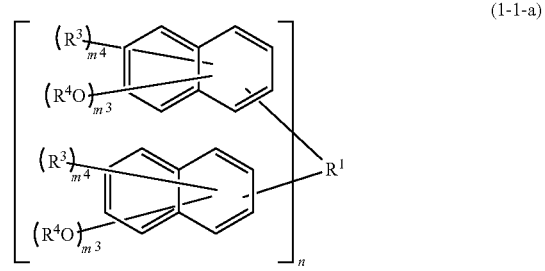

(1-1-a)

In the above formula (1-1-a), $R^1$, $R^3$, $R^4$, n, $m^3$, and $m^4$ are as defined in the above formula (1-1). That is, each $R^4$ is independently an acid dissociation group or a hydrogen atom, and at least one thereof is an acid dissociation group. In the present specification, the "acid dissociation group" refers to a characteristic group that is cleaved in the presence of an acid and thereby converted into an alkali soluble group or the like. Examples of the alkali soluble group include a phenolic hydroxyl group, a carboxyl group, a sulfonic acid group, and a hexafluoroisopropanol group. A phenolic hydroxyl group and a carboxyl group are preferable, and a phenolic hydroxyl group is particularly preferable. The acid dissociation group can be appropriately selected for use from among those proposed in hydroxystyrene based resins, (meth)acrylic acid based resins, etc. used in chemical amplification resist compositions for KrF or ArF. The acid dissociation group preferably has the property of causing chain cleavage reactions in the presence of an acid in order to achieve higher sensitivity and higher resolution pattern formation. Specific examples of the acid dissociation group include a substituted methyl group, a 1-substituted ethyl group, a 1-substituted n-propyl group, a 1-branched alkyl group, a silyl group, an acyl group, a 1-substituted alkoxymethyl group, a cyclic ether group, an alkoxycarbonyl group, and an alkoxycarbonylalkyl group. The acid dissociation group preferably has no crosslinkable functional group.

The substituted methyl group is normally a substituted methyl group of 2 to 20 carbon atoms and is preferably a substituted methyl group of 4 to 18 carbon atoms and more preferably a substituted methyl group of 6 to 16 carbon atoms. Specific examples of the substituted methyl group include a methoxymethyl group, a methylthiomethyl group, an ethoxymethyl group, a n-propoxymethyl group, an isopropoxymethyl group, a n-butoxymethyl group, a t-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1). Examples of $R^2$ in the following formulae (13-1) include a methyl group, an ethyl group, an isopropyl group, a n-propyl group, a t-butyl group, and a n-butyl group.

(13-1)

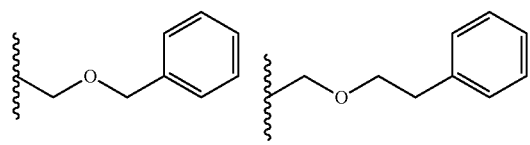

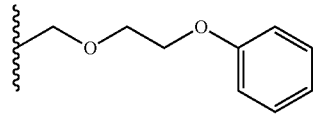

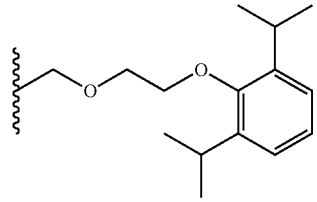

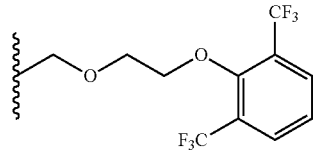

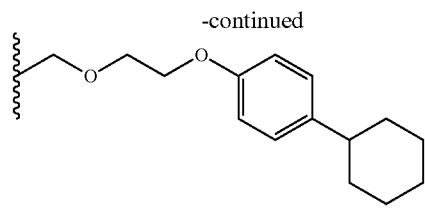

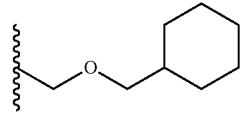

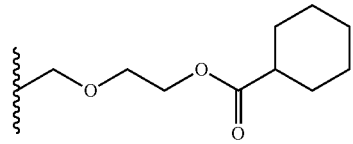

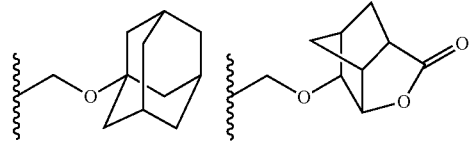

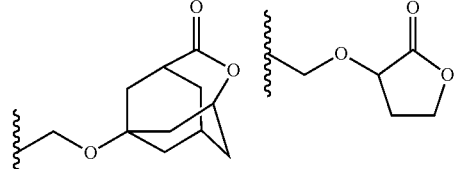

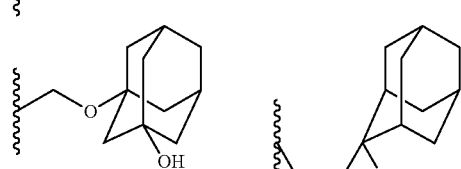

In the formulae (13-1), $R^2$ is an alkyl group of 1 to 4 carbon atoms.

The 1-substituted ethyl group is normally a 1-substituted ethyl group of 3 to 20 carbon atoms and is preferably a 1-substituted ethyl group of 5 to 18 carbon atoms and more preferably a 1-substituted ethyl group of 7 to 16 carbon atoms. Specific examples of the 1-substituted ethyl group include a 1-methoxyethyl group, a 1-methylthioethyl group, a 1,1-dimethoxyethyl group, a 1-ethoxyethyl group, a 1-ethylthioethyl group, a 1,1-diethoxyethyl group, a n-propoxyethyl group, an isopropoxyethyl group, a n-butoxyethyl group, a t-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, and a substituent represented by the following formulae (13-2).

(13-2)

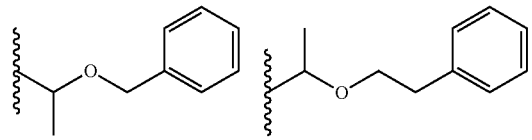

-continued

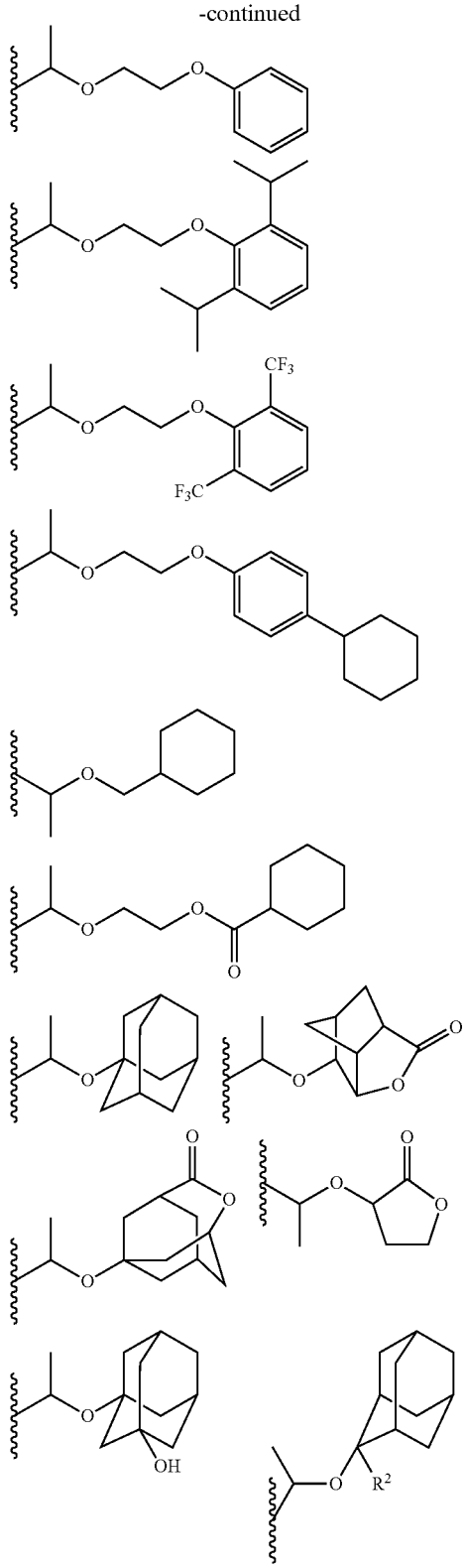

In the formulae (13-2), $R^2$ is as defined in the above formula (13-1).

The 1-substituted n-propyl group is normally a 1-substituted n-propyl group of 4 to 20 carbon atoms and is preferably a 1-substituted n-propyl group of 6 to 18 carbon atoms and more preferably a 1-substituted n-propyl group of 8 to 16 carbon atoms. Specific examples of the 1-substituted n-propyl group include a 1-methoxy-n-propyl group and a 1-ethoxy-n-propyl group.

The 1-branched alkyl group is normally a 1-branched alkyl group of 3 to 20 carbon atoms and is preferably a 1-branched alkyl group of 5 to 18 carbon atoms and more preferably a 1-branched alkyl group of 7 to 16 carbon atoms. Specific examples of the 1-branched alkyl group include an isopropyl group, a sec-butyl group, a tert-butyl group, a 1,1-dimethylpropyl group, a 1-methylbutyl group, a 1,1-dimethylbutyl group, a 2-methyladamantyl group, and a 2-ethyladamantyl group.

The silyl group is normally a silyl group of 1 to 20 carbon atoms and is preferably a silyl group of 3 to 18 carbon atoms and more preferably a silyl group of 5 to 16 carbon atoms. Specific examples of the silyl group include a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group, and a triphenylsilyl group.

The acyl group is normally an acyl group of 2 to 20 carbon atoms and is preferably an acyl group of 4 to 18 carbon atoms and more preferably an acyl group of 6 to 16 carbon atoms. Specific examples of the acyl group include an acetyl group, a phenoxyacetyl group, a propionyl group, a butyryl group, a heptanoyl group, a hexanoyl group, a valeryl group, a pivaloyl group, an isovaleryl group, a lauroyl group, an adamantylcarbonyl group, a benzoyl group, and a naphthoyl group.

The 1-substituted alkoxymethyl group is normally a 1-substituted alkoxymethyl group of 2 to 20 carbon atoms and is preferably a 1-substituted alkoxymethyl group of 4 to 18 carbon atoms and more preferably a 1-substituted alkoxymethyl group of 6 to 16 carbon atoms. Specific examples of the 1-substituted alkoxymethyl group include a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

The cyclic ether group is normally a cyclic ether group of 2 to 20 carbon atoms and is preferably a cyclic ether group of 4 to 18 carbon atoms and more preferably a cyclic ether group of 6 to 16 carbon atoms. Specific examples of the cyclic ether group include a tetrahydropyranyl group, a tetrahydrofuranyl group, a tetrahydrothiopyranyl group, a tetrahydrothiofuranyl group, a 4-methoxytetrahydropyranyl group, and a 4-methoxytetrahydrothiopyranyl group.

The alkoxycarbonyl group is normally an alkoxycarbonyl group of 2 to 20 carbon atoms and is preferably an alkoxycarbonyl group of 4 to 18 carbon atoms and more preferably an alkoxycarbonyl group of 6 to 16 carbon atoms. Specific examples of the alkoxycarbonyl group include a methoxycarbonyl group, an ethoxycarbonyl group, a n-propoxycarbonyl group, an isopropoxycarbonyl group, a n-butoxycarbonyl group, a tert-butoxycarbonyl group, and an acid dissociation group represented by the following formulae (13-3) wherein n=0.

The alkoxycarbonylalkyl group is normally an alkoxycarbonylalkyl group of 2 to 20 carbon atoms and is preferably an alkoxycarbonylalkyl group of 4 to 18 carbon atoms and more preferably an alkoxycarbonylalkyl group of 6 to 16 carbon atoms. Specific examples of the alkoxycarbonylalkyl group include a methoxycarbonylmethyl group, an ethoxycarbonylmethyl group, a n-propoxycarbonylmethyl group, an isopropoxycarbonylmethyl group, a n-butoxycarbonylmethyl group, and an acid dissociation group represented by the following formulae (13-3) wherein n=1 to 4.

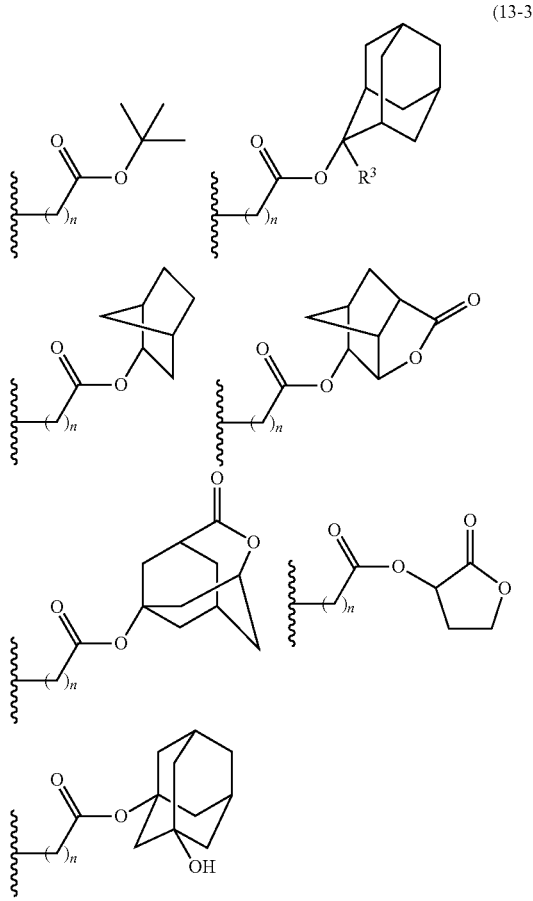

(13-3)

In the formulae (13-3), R³ is a hydrogen atom or a linear or branched alkyl group of 1 to 4 carbon atoms, and n is an integer of 0 to 4.

Among these acid dissociation groups, a substituted methyl group, a 1-substituted ethyl group, a 1-substituted alkoxymethyl group, a cyclic ether group, an alkoxycarbonyl group, and an alkoxycarbonylalkyl group are preferable. A substituted methyl group, a 1-substituted ethyl group, an alkoxycarbonyl group, and an alkoxycarbonylalkyl group are more preferable because of high sensitivity. An acid dissociation group having at least one of structure selected from the group consisting of cycloalkane of 3 to 12 carbon atoms, lactone, and an aromatic ring of 6 to 12 carbon atoms is still more preferable. The cycloalkane of 3 to 12 carbon atoms may be monocyclic or polycyclic and is preferably polycyclic. Specific examples of the cycloalkane of 3 to 12 carbon atoms include monocycloalkane, bicycloalkane, tricycloalkane, and tetracycloalkane and more specifically include: monocycloalkane such as cyclopropane, cyclobutane, cyclopentane, and cyclohexane; and polycycloalkane such as adamantane, norbornane, isobornane, tricyclodecane, and tetracyclodecane. Among them, adamantane, tricyclodecane, and tetracyclodecane are preferable, and adamantane and tricyclodecane are particularly preferable. The cycloalkane of 3 to 12 carbon atoms may have a substituent.

Examples of the lactone include butyrolactone and a cycloalkane group of 3 to 12 carbon atoms having a lactone group. Examples of the aromatic ring of 6 to 12 carbon atoms include a benzene ring, a naphthalene ring, an anthracene ring, a phenanthrene ring, and a pyrene ring. A benzene ring and a naphthalene ring are preferable, and a naphthalene ring is particularly preferable.

As the acid dissociation group, particularly, an acid dissociation group selected from the group consisting of each group represented by the following formulae (13-4) is preferable because of high resolution.

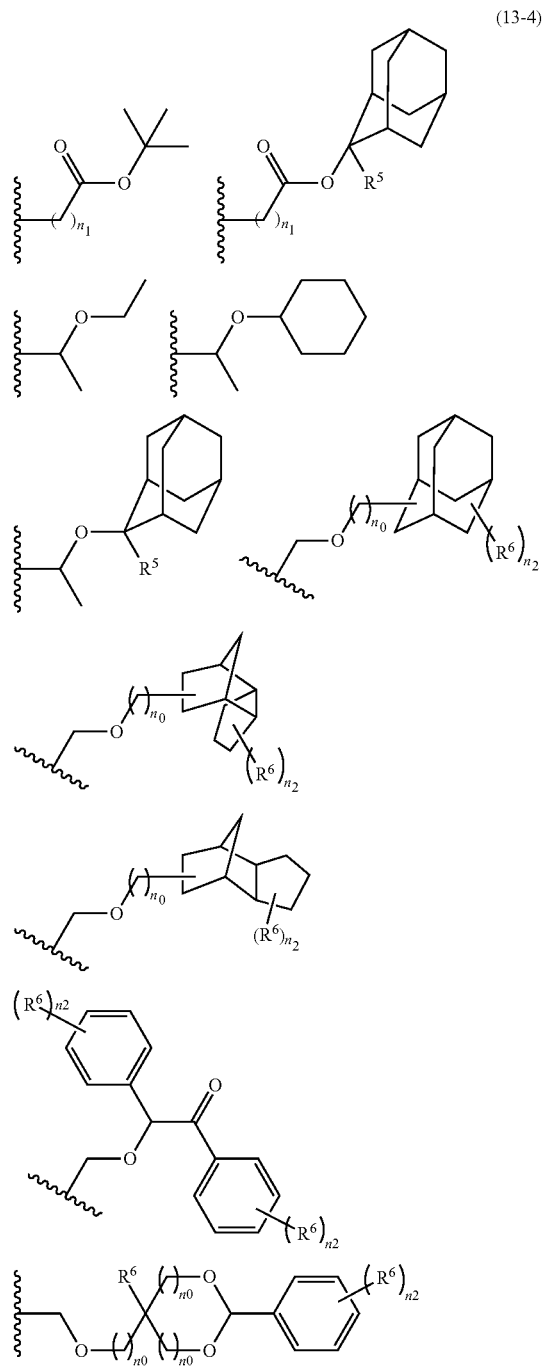

(13-4)

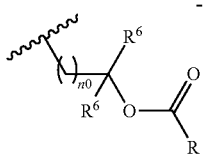

In the formulae (13-4), $R^5$ is a hydrogen atom or a linear or branched alkyl group of 1 to 4 carbon atoms; each $R^6$ is independently a hydrogen atom, a linear or branched alkyl group of 1 to 4 carbon atoms, a cyano group, a nitro group, a heterocyclic group, a halogen atom, or a carboxyl group; $n_1$ is an integer of 0 to 4; each $n_2$ is independently an integer of 1 to 5; and each no is independently an integer of 0 to 4.

In the present embodiment, in terms of sensitivity as a resist composition, the compound represented by the above formula (1-1) is preferably a compound represented by the following formula (1-2).

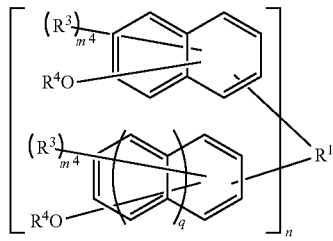

(1-2)

In the formula (1-2), $R^1$, $R^3$, $R^4$, $m^4$, n, and q are as defined in the above formula (1-1).

The compound represented by the above formula (1-2) is more preferably a compound represented by the formula (1-2) wherein q is 1, i.e., a compound represented by the following formula (1-2-a):

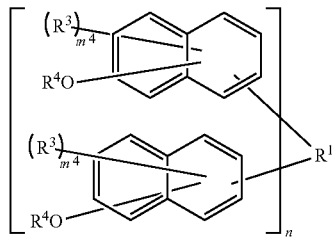

(1-2-a)

In the formula (1-2-a), $R^1$, $R^3$, $R^4$, $m^4$, and n are as defined in the above formula (1-2).

In terms of solubility and sensitivity as a resist composition, the compound represented by the above formula (1-1) is preferably a compound of the above formula (1-1) wherein $m^3$ is 2.

In terms of resist characteristics such as heat resistance, sensitivity, resolution, and roughness, the compound represented by the above formula (1-1) is preferably a compound of the above formula (1-1) wherein n is 1.

In terms of solubility, the compound represented by the above formula (1-1) is more preferably a compound represented by the following formula (1-3).

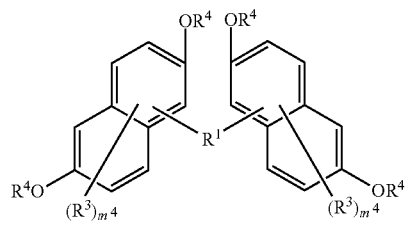

(1-3)

In the formula (1-3), $R^1$, $R^3$, $R^4$, and $m^4$ are as defined in the above formula (1-1).

In the present embodiment, the compound represented by the above formula (1) is preferably a compound represented by the following formula (3).

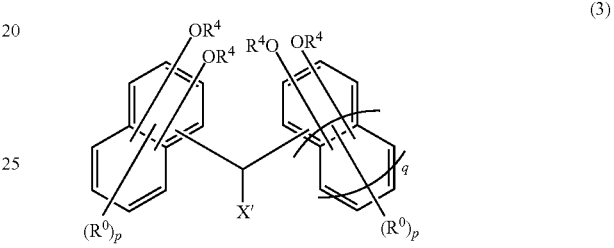

(3)

In the formula (3), X' is a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; $R^4$ is as defined in the above formula (1-1); each p is independently an integer of 0 to 5; and q is 0 or 1.

The compound represented by the above formula (3) is preferably a compound represented by the following formula (3-1).

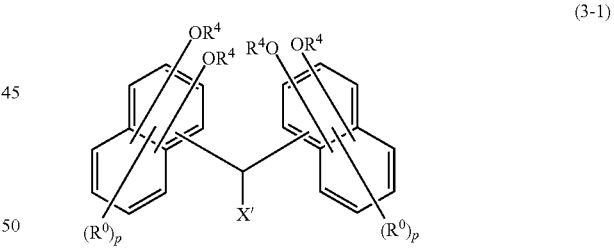

(3-1)

In the formula (3-1), X' is a hydrogen atom or a C1-18 monovalent substituent; each $R^0$ is independently a C1-4 alkyl group or a halogen atom and may be the same as or different from each other on the same naphthalene ring; $R^4$ is as defined in the above formula (1-1); and each p is independently an integer of 0 to 5.

The substituent of 1 to 18 carbon atoms in X' is preferably, for example, a monovalent hydrocarbon group which may have a heteroatom, and may be a monovalent hydrocarbon group having no heteroatom. This hydrocarbon group is preferably a monovalent hydrocarbon group having an aromatic ring. Examples of such a hydrocarbon group include a biphenyl group, a phenyl group, a naphthyl group, an anthracene group, and a pyrene group (hereinafter the same). Among them, a biphenyl group is preferable.

Specific examples of the compound represented by the above formula (1) can include, but not limited to, the followings:
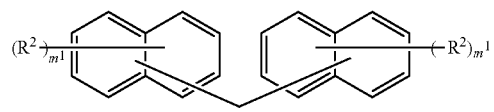
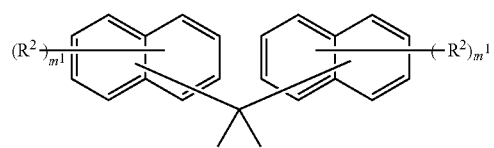
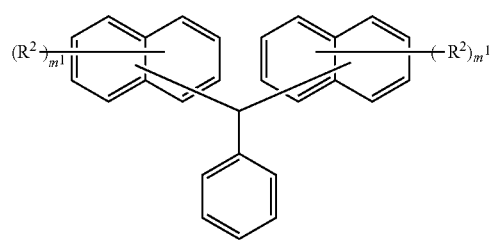
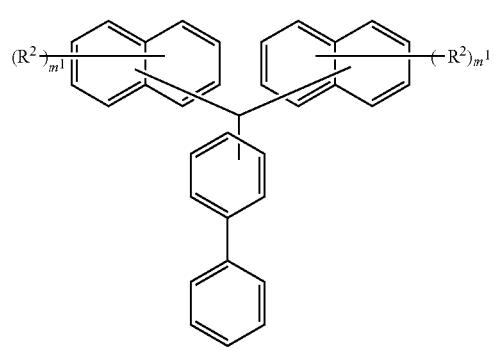
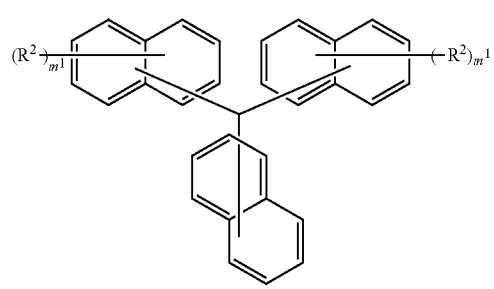
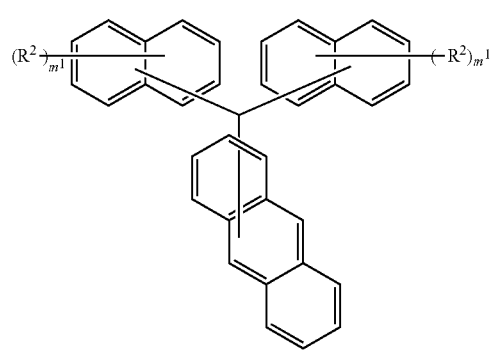
-continued
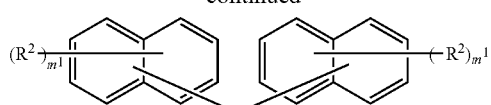
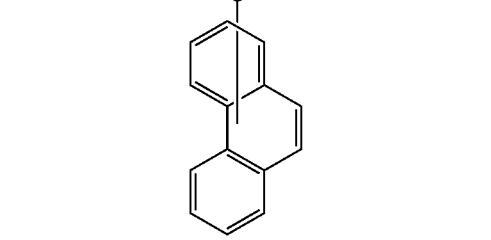
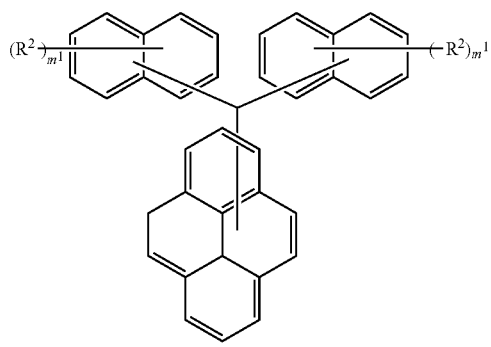
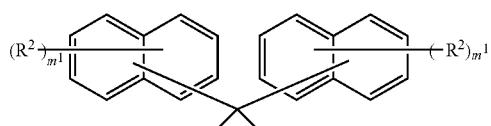
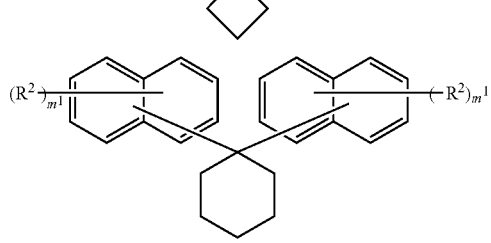
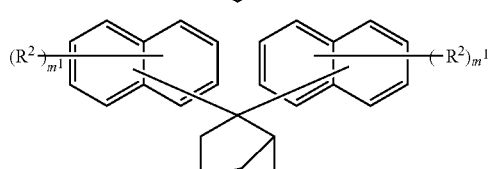
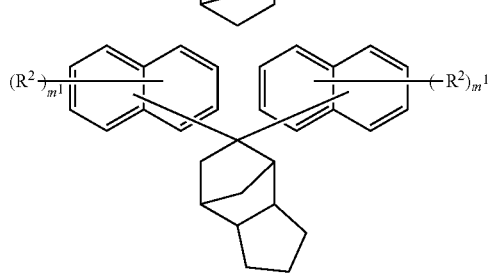
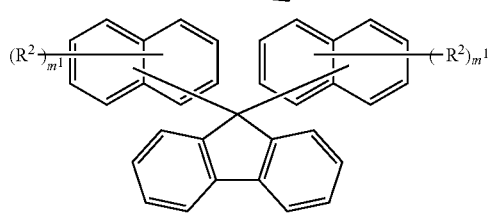

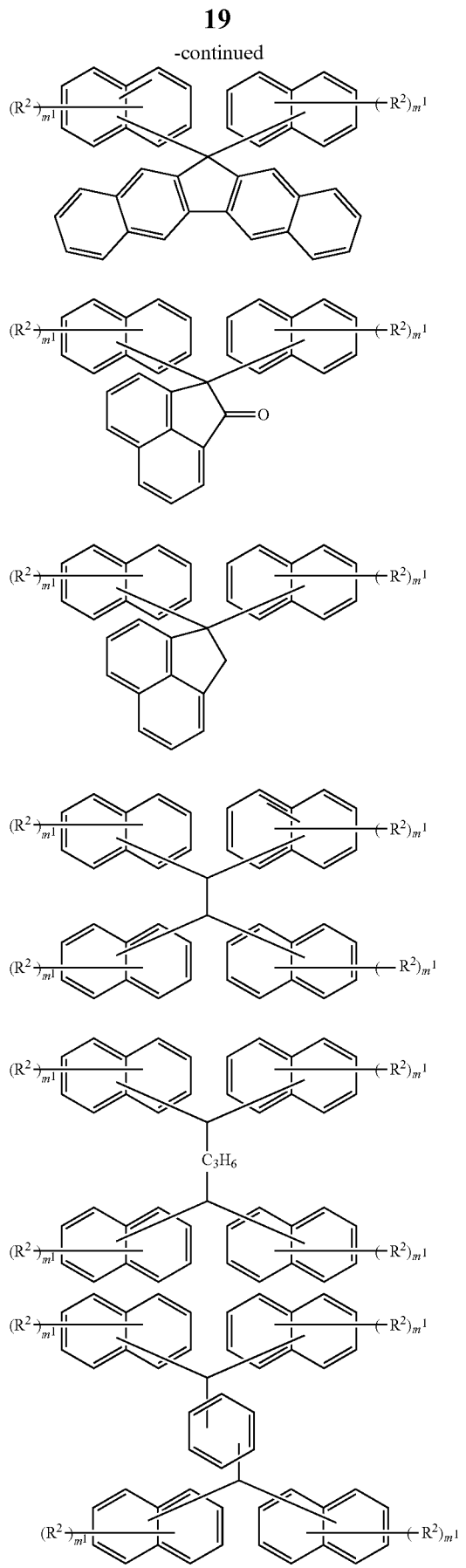

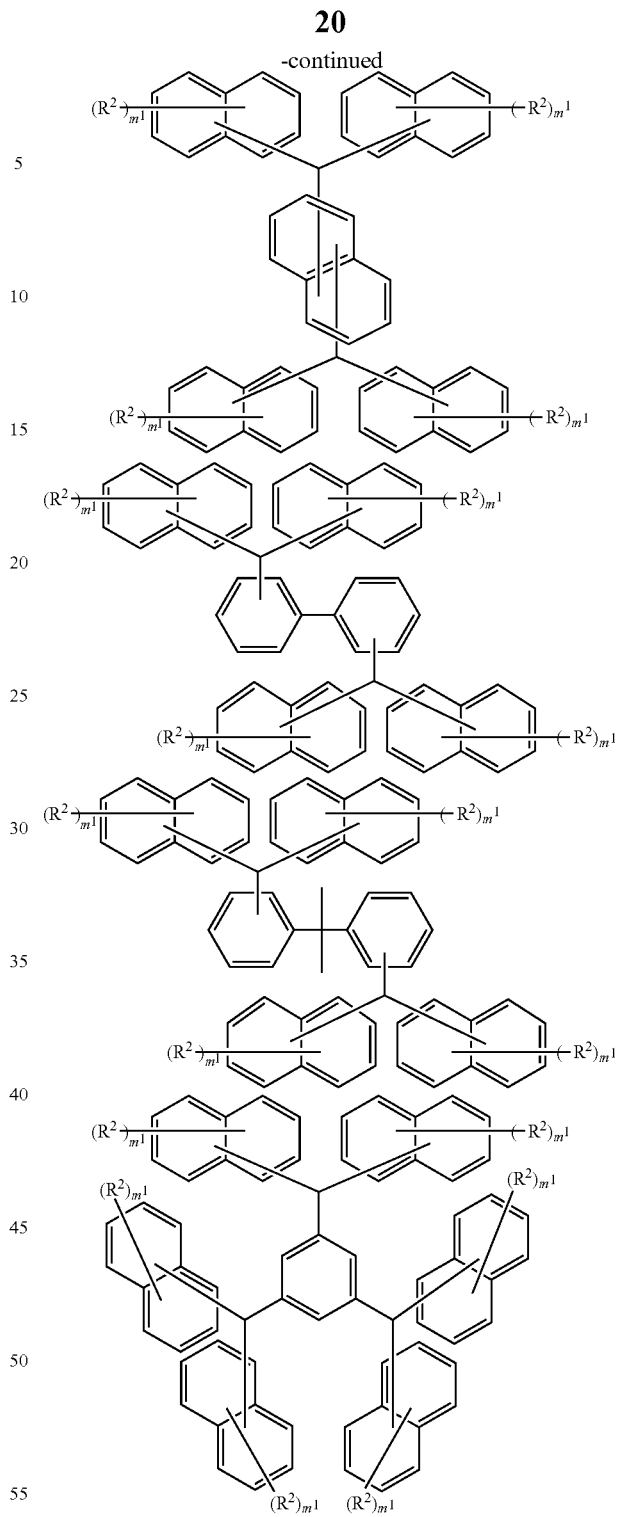

In the formulae, $R^2$ and $m^1$ are as defined in the above formula (1).

A method for producing the compound represented by the above formula (1) according to the present embodiment is not particularly limited. For example, the compound represented by the above formula (1) wherein q=1 is obtained by reacting a naphthol compound or a thionaphthol compound with a corresponding aldehyde compound or ketone compound in the presence of an acid catalyst to obtain a polyphenol compound, and introducing an acid dissociation group to at least one phenolic hydroxyl group of the polyphenol compound by a publicly known method. The compound represented by the above formula (1) wherein q=0 can be synthesized similarly by using the naphthol compound or the thionaphthol compound in combination with a phenol compound or a thiophenol compound.

Examples of the naphthol compound include, but not particularly limited to, naphthol, methylnaphthol, methoxynaphthol, and naphthalenediol. Among them, naphthalenediol is more preferably used because a xanthene structure can be easily obtained.

Examples of the above thionaphthol compound include, but not particularly limited to, naphthalenethiol, methylnaphthalenethiol, methoxynaphthalenethiol, and naphthalenedithiol.

Examples of the phenol compound include, but not particularly limited to, phenol, methylphenol, methoxybenzene, catechol, resorcinol, hydroquinone, and trimethylhydroquinone.

Examples of the thiophenol compound include, but not particularly limited to, benzenethiol, methylbenzenethiol, methoxybenzenethiol, benzenedithiol, and trimethylbenzenedithiol.

Examples of the aldehyde compound include, but not particularly limited to, formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, bis(diformylphenyl)methane, bis(diformylphenyl)propane, and benzenetricarboxaldehyde. Among them, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, and benzenetricarboxaldehyde are preferable in terms of providing high heat resistance.

Examples of the above ketone compound include, but not particularly limited to, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferable in terms of providing high heat resistance.

The above acid catalyst is not particularly limited and can be appropriately selected from well known inorganic acids and organic acids. Examples of acid catalyst include: inorganic acids such as hydrochloric acid, sulfuric acid, phosphoric acid, hydrobromic acid, and hydrofluoric acid; organic acids such as oxalic acid, formic acid, p-toluenesulfonic acid, methanesulfonic acid, trifluoroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. From the viewpoint of production such as easy availability and handleability, the acid catalyst is preferably hydrochloric acid or sulfuric acid. The acid catalyst can be used alone or in combination of two or more.

Upon producing the compound represented by the above formula (1), a reaction solvent may be used. The reaction solvent is not particularly limited as long as the reaction of the aldehyde compound or the ketone compound used with the naphthol compound or the thionaphthol compound proceeds. As the reaction solvent, for example, water, methanol, ethanol, propanol, butanol, tetrahydrofuran, dioxane, or a mixed solvent thereof can be used. The amount of the reaction solvent used is not particularly limited and is within the range of, for example, from 0 or more parts by mass to 2000 or less parts by mass based on 100 parts by mass of the reaction raw materials.

Upon producing the above polyphenol compound, the reaction temperature is not particularly limited and can be appropriately selected according to the reactivity of the reaction raw materials. The reaction temperature is preferably within the range from 10° C. or higher to 200° C. or lower. For highly selectively synthesizing the compound represented by the above formula (1) of the present embodiment, a lower temperature is more effective, and the range from 10° C. or higher to 60° C. or lower is more preferable.

Examples of the method for producing the above polyphenol compound include, but not particularly limited to, a method of charging the naphthol compound or the thionaphthol compound, the aldehyde compound or the ketone compound, and the acid catalyst at once, and a method of dropping the naphthol compound or the thionaphthol compound and the aldehyde compound or the ketone compound in the presence of the acid catalyst. After the polycondensation reaction for obtaining the polyphenol compound terminates, the temperature of the reaction vessel is elevated to from 130° C. or higher to 230° C. or lower in order to remove unreacted raw materials and acid catalyst, etc. present in the system, and volatile components can also be removed at about 1 to 50 mmHg.

Upon producing the above polyphenol compound, the ratio of each raw material is not particularly limited. For example, 2 mol to an excess of the naphthol compound or the thionaphthol compound and from 0.001 or more mol to 1 or less mol of the acid catalyst based on 1 mol of the aldehyde compound or the ketone compound may be used. The polycondensation reaction for obtaining the polyphenol compound proceeds by reacting each raw material at from 20° C. or higher to 60° C. or lower at normal pressure for about 20 minutes to 100 hours.

Upon producing the above polyphenol compound, the target component can be isolated by a publicly known method after the reaction terminates. The method for isolating the target component is not particularly limited. For example, the method can involve concentrating the reaction solution, precipitating the reaction product by the addition of pure water, cooling the reaction solution to room temperature, then separating solid by filtration, subsequently filtering and drying the obtained solid, then separating and purifying the solid from by-products by column chromatography, and distilling off the solvent, followed by filtration and drying to obtain the objective compound.

The method for introducing an acid dissociation group to at least one phenolic hydroxyl group of the polyphenol compound is publicly known. For example, an acid dissociation group can be introduced to at least one phenolic hydroxyl group of the polyphenol compound as described below. The compound for introducing an acid dissociation group may be synthesized by a publicly known method or may be obtained as a commercially available product. Examples of such a compound include, but not particularly limited to, active carboxylic acid derivatives such as acid chloride, acid anhydride, and dicarbonate, alkyl halide, vinyl alkyl ether, dihydropyran, and halocarboxylic acid alkyl ester.

For example, the polyphenol compound is dissolved or suspended in an aprotic solvent such as acetone, tetrahydrofuran (THF), and propylene glycol monomethyl ether acetate. Vinyl alkyl ether (e.g., ethyl vinyl ether) or dihydropyran is added thereto and reacted at from 20° C. or higher to 60° C. or lower at normal pressure for 6 to 72 hours in the presence of an acid catalyst such as pyridinium p-toluenesulfonate. The obtained reaction solution is neutralized with an alkali compound and added to distilled water to precipitate white solid, and the separated white solid can then be washed with distilled water and dried to obtain the compound represented by the formula (1).

In another method, the polyphenol compound is dissolved or suspended in an aprotic solvent such as acetone, THF, and propylene glycol monomethyl ether acetate. Alkyl halide such as ethyl chloromethyl ether or halocarboxylic acid alkyl ester such as methyladamantyl bromoacetate is added thereto and reacted at from 20° C. or higher to 110° C. or lower at normal pressure for 6 to 72 hours in the presence of an alkali catalyst such as potassium carbonate. The obtained reaction solution is neutralized with an acid such as hydrochloric acid and added to distilled water to precipitate white solid, and the separated white solid can then be washed with distilled water and dried to obtain the compound represented by the formula (1).

(Composition of Second Aspect)

According to the second aspect of the present embodiment, the resist composition contains a compound represented by the following formula (2).

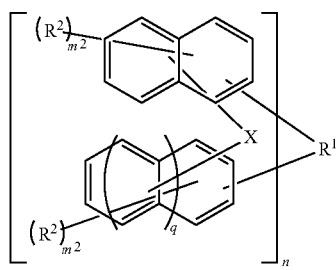

(2)

In the formula (2), each X is independently an oxygen atom or a sulfur atom; $R^1$ is a single bond or a C1-30 2n-valent hydrocarbon group wherein the hydrocarbon group may have a cyclic hydrocarbon group (except for an aromatic group), a double bond, a heteroatom, or a C6-30 aromatic group; each $R^2$ is independently a hydrogen atom, a halogen atom, a C1-10 linear, branched, or cyclic alkyl group, a C6-10 aryl group, a C2-10 alkenyl group, a hydroxyl group, or a group in which a hydrogen atom of a hydroxyl group is substituted with an acid dissociation group, and may be the same as or different from each other on the same naphthalene ring or benzene ring; at least one of $R^2$ is a group in which a hydrogen atom of a hydroxyl group is substituted with an acid dissociation group; the structural formulas of the repeating units in the formula (2) may be the same as or different from each other; each $m^2$ is independently an integer of 1 to 6; and n is an integer of 1 to 4.

each q is independently 0 or 1 and are preferably 1. That is, the compound represented by the above formula (2) is preferably represented by the following formula (2-a).

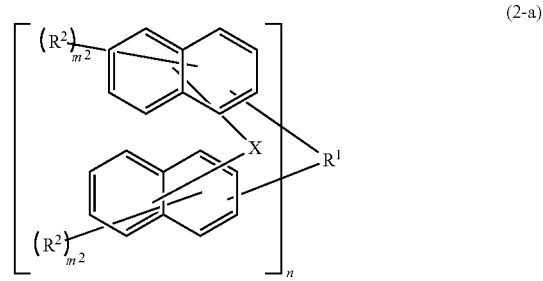

(2-a)

In the formula (2-a), $R^1$, $R^2$, X, $m^1$, and n are as defined in the above formula (2).

The above 2n-valent hydrocarbon group is as defined in the above compound represented by the formula (1).

In the compound represented by the above formula (2), in terms of prevention of equipment contamination upon resist film exposure, X is preferably an oxygen atom. In terms of solubility in a safe solvent and resist pattern characteristics, the compound represented by the formula (2) is preferably a compound represented by the following formula (2-1).

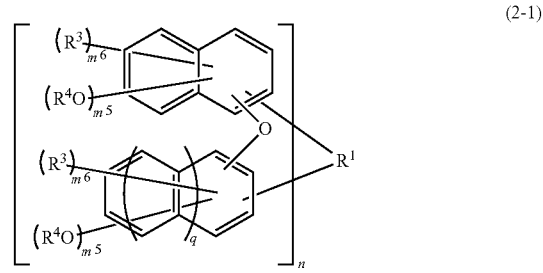

(2-1)

In the formula (2-1), $R^1$, $R^3$, $R^4$, n, and q are as defined in the above formula (1-1); each $m^5$ is independently an integer of 1 to 6; each $m^6$ is independently an integer of 0 to 5; and each $m^5+m^6$ is independently an integer of 1 to 6.

each q is independently 0 or 1 and are more preferably 1. That is, the compound represented by the above formula (2-1) is more preferably a compound represented by the following formula (2-1-a).

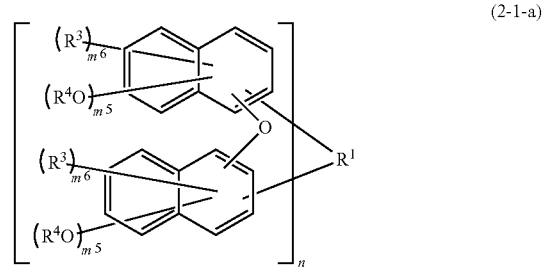

(2-1-a)

In the formula (2-1-a), $R^1$, $R^3$, $R^4$, n, $m^5$, and $m^6$ are as defined in the above formula (2-1).

In terms of sensitivity as a resist composition, the compound represented by the above formula (2-1) is more preferably a compound represented by the following formula (2-2).

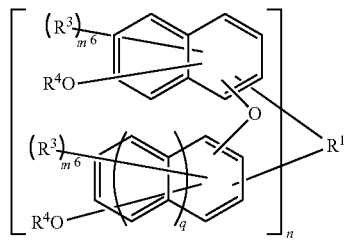

(2-2)

In the formula (2-2), $R^1$, $R^3$, $R^4$, $m^6$, n, and q are as defined in the above formula (2-1).

q is more preferably 1. That is, the compound represented by the above formula (2-2) is more preferably a compound represented by the following formula (2-2-a).

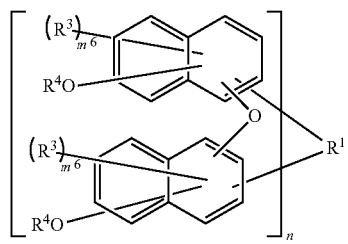

(2-2-a)

In the formula (2-2-a), $R^1$, $R^3$, $R^4$, $m^6$, and n are as defined in the above formula (2-2).

In terms of solubility and sensitivity as a resist composition, $m^5$ in the above formula (2-1) is preferably 2.

In terms of resist characteristics such as heat resistance, sensitivity, resolution, and roughness, the compound represented by the above formula (2-1) is preferably a compound of the above formula (2-1) wherein n is 1.

In terms of solubility, the compound represented by the above formula (2-1) is more preferably a compound represented by the following formula (2-3).

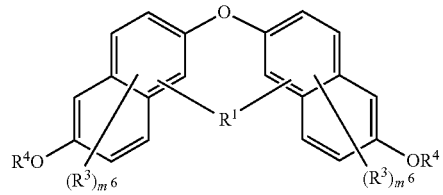

(2-3)

In the formula (2-3), $R^1$, $R^3$, $R^4$, and $m^6$ are as defined in the above formula (2-1).

In the present embodiment, the compound represented by the above formula (2) is preferably a compound represented by the following formula (4).

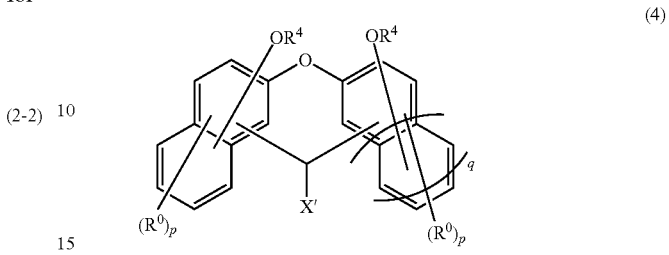

(4)

In the formula (4), X' is a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; $R^4$ is as defined in the above formula (2-1); each p is independently an integer of 0 to 5; and q is 0 or 1.

The compound represented by the above formula (4) is preferably a compound represented by the following formula (4-1).

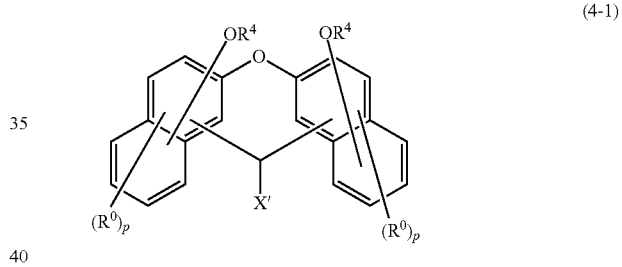

(4-1)

In the formula (4-1), X' is a hydrogen atom or a C1-18 monovalent substituent; each $R^0$ is independently a C1-4 alkyl group or a halogen atom and may be the same as or different from each other on the same naphthalene ring; $R^4$ is as defined in the above formula (4); and each p is independently an integer of 0 to 5.

Specific examples of the compound represented by the above formula (2) can include, but not limited to, the followings:

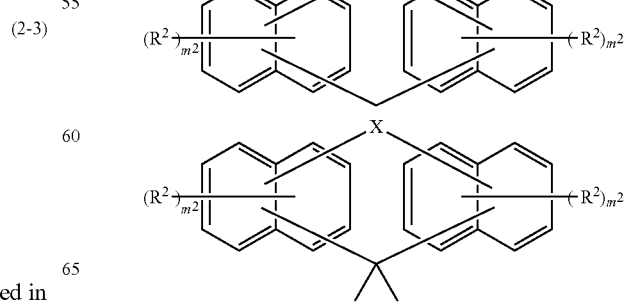

-continued
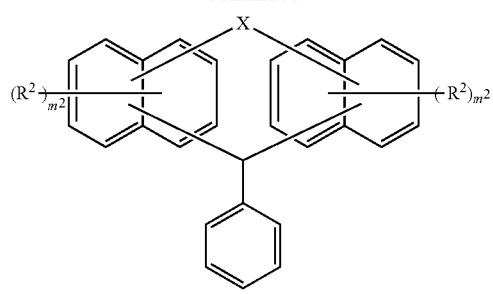
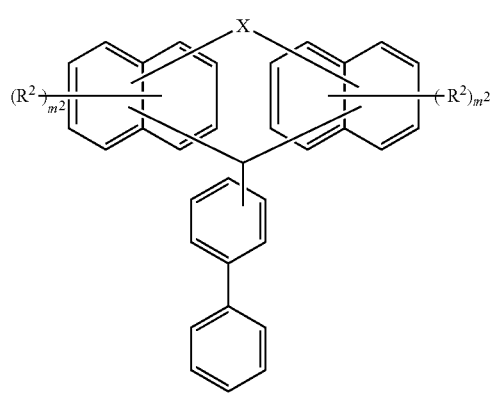
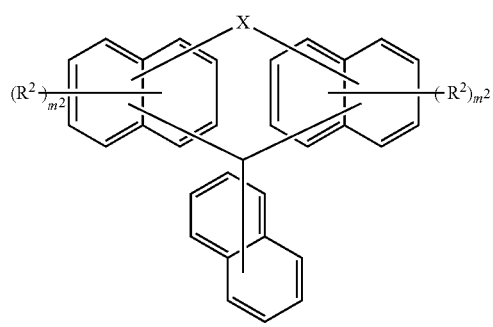
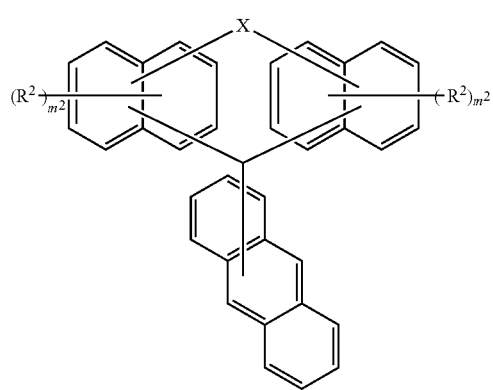
-continued
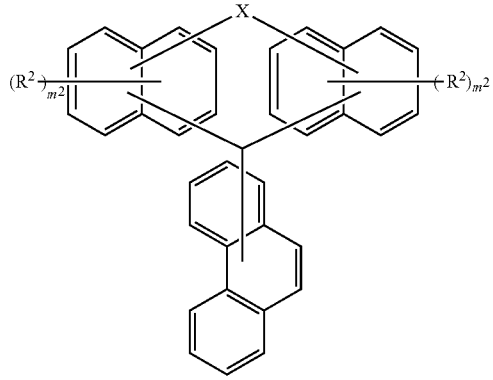
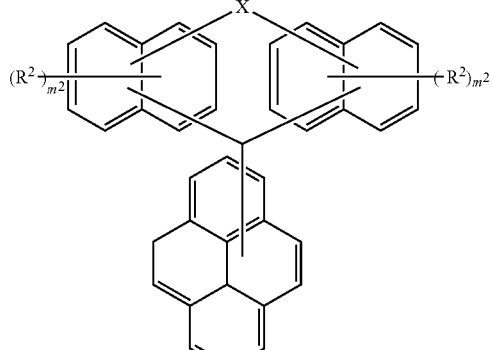
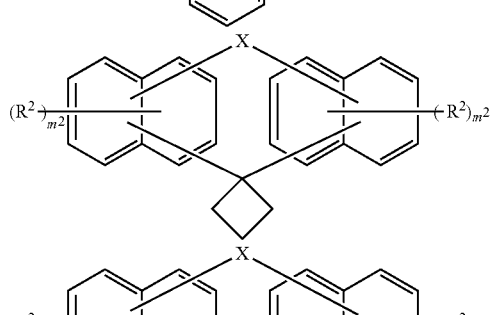
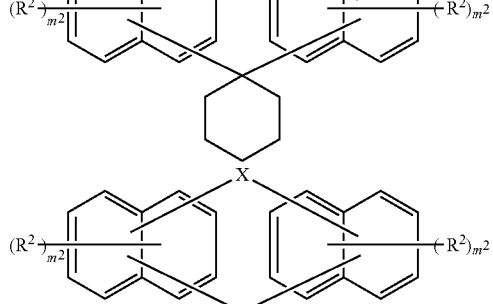
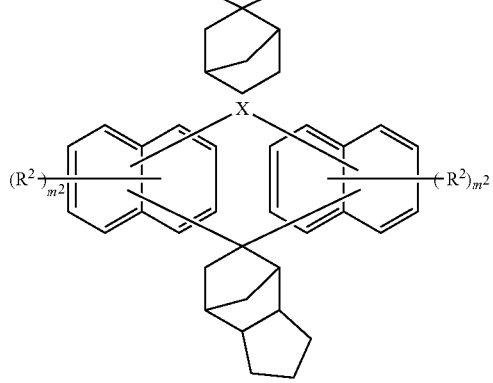

-continued
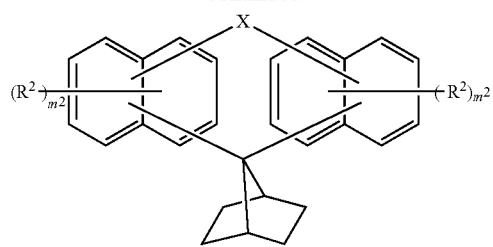
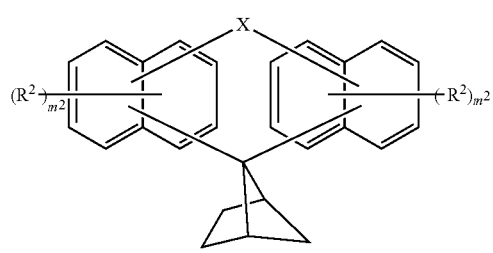
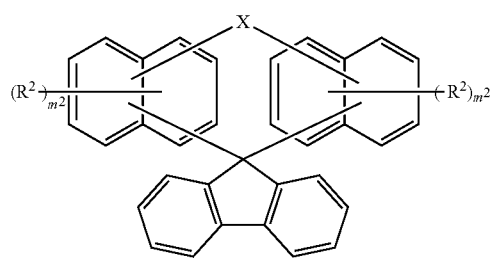
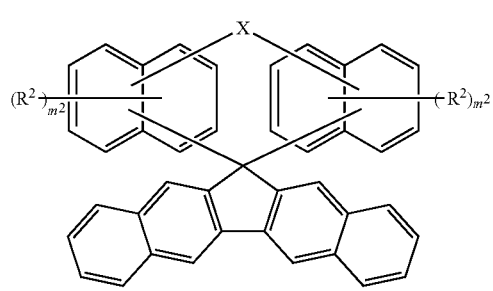
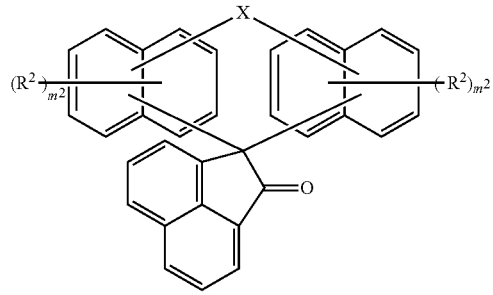
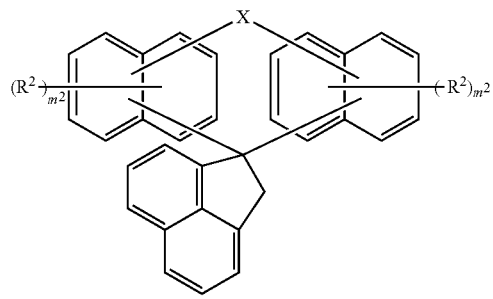
-continued
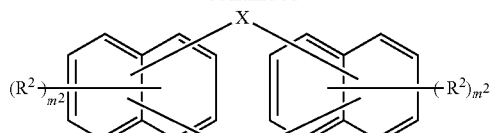
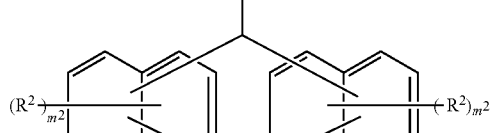
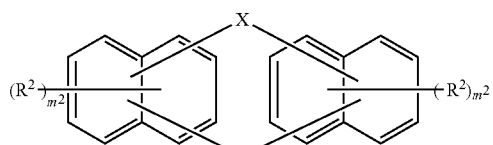
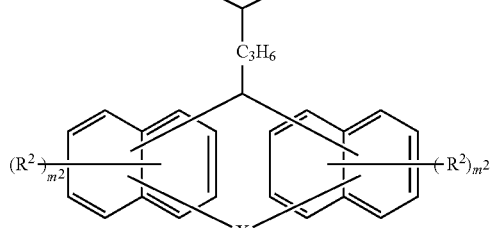
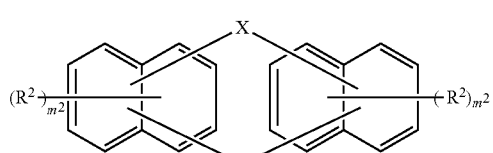
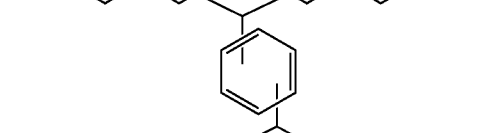
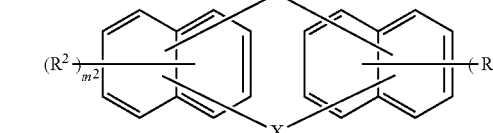
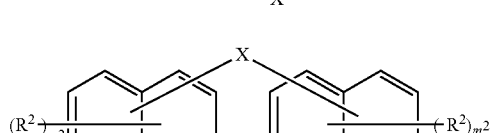
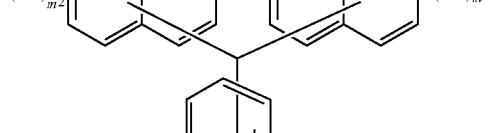
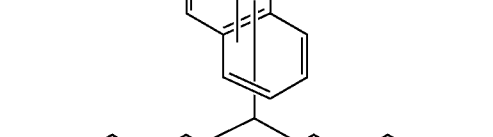
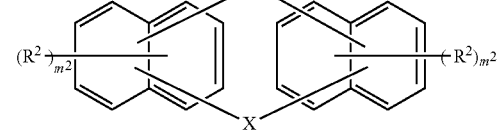

-continued

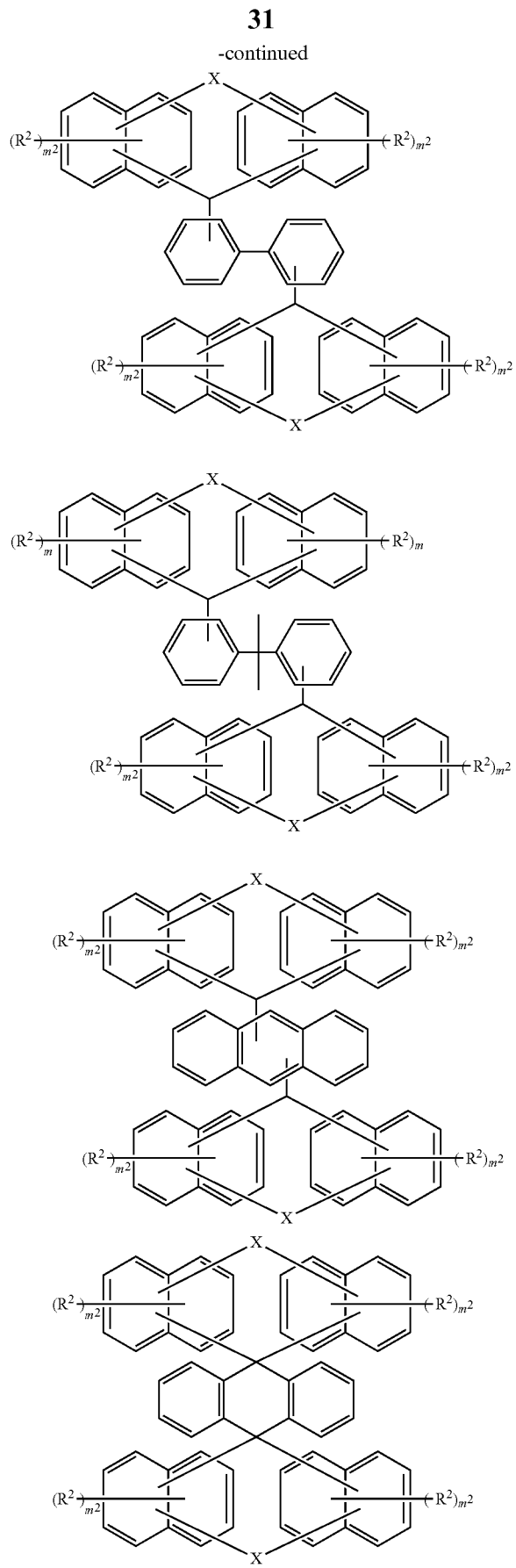

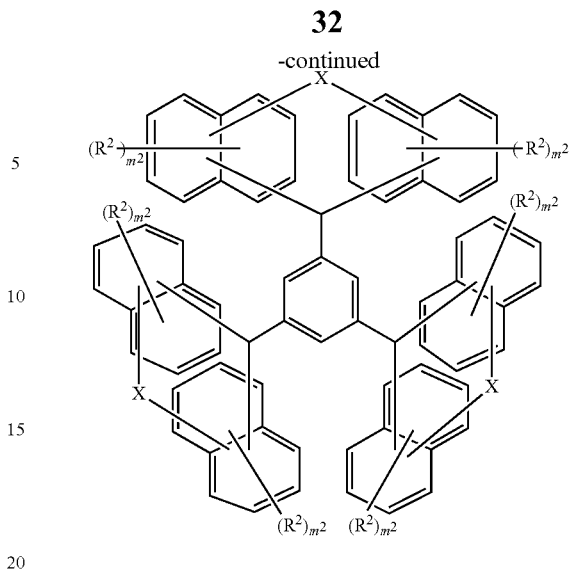

In the formulae, $R^2$, X, and $m^2$ are as defined in the above formula (2).

The compound represented by the above formula (2) can be obtained in the same way as in the compound represented by the above formula (1), and the compound represented by the above formula (2) wherein q=1 is obtained by reacting a naphthol compound or a thionaphthol compound with a corresponding aldehyde compound or ketone compound in the presence of an acid catalyst to obtain a polyphenol compound, and introducing an acid dissociation group to at least one phenolic hydroxyl group of the polyphenol compound by a publicly known method. The compound represented by the above formula (2) wherein q=0 can be synthesized similarly by using the naphthol compound or the thionaphthol compound in combination with a phenol compound or a thiophenol compound. The description about each raw material, synthesis conditions, and isolation methods overlaps with the description made in the compound represented by the above formula (1) and is therefore omitted here.

(Physical Properties, Etc. Of Resist Composition)

The resist composition of the present embodiment can form an amorphous film as a resist film by spin coating. Depending on the kind of the developing solution used, any of a positive type resist pattern and a negative type resist pattern can be selectively prepared.

In the case of a positive type resist pattern, the dissolution rate of the amorphous film formed by spin coating with the resist composition of the present embodiment in a developing solution at 23° C. is preferably 5 angstrom/sec or less, more preferably from 0.05 angstrom/sec or more to 5 angstrom/sec or less, and still more preferably from 0.0005 angstrom/sec or more to 5 angstrom/sec or less. When this dissolution rate is 5 angstrom/sec or less, the amorphous film is less likely to dissolve in a developing solution, and can form a resist more securely. When the amorphous film has the dissolution rate of 0.0005 angstrom/sec or more, the resolution may be improved. It is presumed that this is because due to the change in the solubility before and after exposure of the compound represented by the above formula (1) or (2), contrast at the interface between the exposed portion being dissolved in a developing solution and the unexposed portion not being dissolved in a developing solution is increased. When the dissolution rate is 0.0005 angstrom/sec or more, reduction effects of line edge roughness (hereinafter, referred to as "LER") and reduction effects of defect are further enhanced.

In the case of a negative type resist pattern, the dissolution rate of the amorphous film formed by spin coating with the resist composition of the present embodiment in a developing solution at 23° C. is preferably 10 angstrom/sec or more. When this dissolution rate is 10 angstrom/sec or more, the amorphous film more easily dissolves in a developing solution, and is suitably used for a resist. When the amorphous film has the dissolution rate of 10 angstrom/sec or more, the resolution may be improved. It is presumed that this is because the micro surface portion of the compound represented by the above formula (1) or (2) dissolves and LER is reduced. When the dissolution rate is 10 angstrom/sec or more, reduction effects of defect are further enhanced.

The dissolution rate can be determined by dipping the amorphous film in the developing solution at 23° C. for a predetermined time, and measuring film thicknesses before and after dipping according to a publicly known method such as visual observation, an ellipsometer, or a QCM method.

In the case of a positive type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 10 angstrom/sec or more. When this dissolution rate is 10 angstrom/sec or more, the amorphous film more easily dissolves in a developing solution, and is suitably used for a resist. When the amorphous film has the dissolution rate of 10 angstrom/sec or more, the resolution may be improved. It is presumed that this is because the micro surface portion of the compound represented by the above formula (1) or (2) dissolves and LER is reduced. When the dissolution rate is 10 angstrom/sec or more, reduction effects of defect are further enhanced.

In the case of a negative type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably from 0.05 angstrom/sec or more to 5 angstrom/sec or less, and still more preferably from 0.0005 angstrom/sec or more to 5 angstrom/sec or less. When this dissolution rate is 5 angstrom/sec or less, the amorphous film is less likely to dissolve in a developing solution, and can form a resist more securely. When the amorphous film has the dissolution rate of 0.0005 angstrom/sec or more, the resolution may be improved. It is presumed that this is because due to the change in the solubility before and after exposure of the compound represented by the above formula (1) or (2), contrast at the interface between the unexposed portion being dissolved in a developing solution and the exposed portion not being dissolved in a developing solution is increased. When the dissolution rate is 0.0005 angstrom/sec or more, reduction effects of LER and reduction effects of defect are further enhanced.

(Other Components of Resist Composition)

The resist composition of the present embodiment contains the compound represented by the above formula (1) or the compound represented by the above formula (2) as a solid component. The resist composition of the present embodiment may contain both of the compound represented by the above formula (1) and the compound represented by the above formula (2).

The resist composition of the present embodiment preferably further contains a solvent, in addition to the compound represented by the above formula (1) or (2).

Examples of the solvent used in the present embodiment include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate (PGMEA), propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as methyl ethyl ketone, 2-heptanone, 3-heptanone, 4-heptanone, cyclopentanone (CPN), and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more.

The solvent used in the present embodiment is preferably a safe solvent, more preferably at least one selected from the group consisting of PGMEA, PGME, CHN, CPN, 2-heptanone, anisole, butyl acetate, ethyl propionate, and ethyl lactate, and still more preferably at least one selected from the group consisting of PGMEA, PGME, and CHN.

The content of the solid component and the content of the solvent in the resist composition are not particularly limited. Preferably, the content of the solid component is from 1% by mass or more to 80% by mass or less based on 100% by mass of the total content of the solid component, and the content of the solvent is from 20% by mass or more to 99% by mass or less based thereon. More preferably, the content of the solid component is from 1% by mass or more to 50% by mass or less based on 100% by mass of the total content of the solid component, and the content of the solvent is from 50% by mass or more to 99% by mass or less based thereon. Still more preferably, the content of the solid component is from 2% by mass or more to 40% by mass or less based on 100% by mass of the total content of the solid component, and the content of the solvent is from 60% by mass or more to 98% by mass or less based thereon. Particularly preferably, the content of the solid component is from 2% by mass or more to 10% by mass or less based on 100% by mass of the total content of the solid component, and the content of the solvent is from 90% by mass or more to 98% by mass or less based thereon.

The resist composition of the present embodiment may contain, as a solid component other than above, at least one selected from the group consisting of an acid generating agent, an acid diffusion controlling agent, and other solid components.

The content of the compound represented by the above formula (1) or (2) used in the present embodiment is not particularly limited and is preferably from 50% by mass or more to 99.4% by mass or less based on the total mass of the solid component (summation of optionally used solid component such as compound represented by the formula (1), compound represented by the formula (2), acid generating agent, acid diffusion controlling agent, and other solid components, hereinafter the same), more preferably from 55% by mass or more to 90% by mass or less, still more preferably from 60% by mass or more to 80% by mass or less, and particularly preferably from 60% by mass or more to 70% by mass or less. In the case of the content within the above range, resolution is further improved, and LER is further decreased.

When the resist composition contains both of the compound represented by the above formula (1) and the compound represented by the above formula (2), the content of the compound represented by the above formula (1) or (2) is the total amount of the compound represented by the above formula (1) and the compound represented by the above formula (2).

The resist composition of the present embodiment preferably contains one or more acid generating agents generating an acid directly or indirectly by irradiation of any radiation selected from visible light, ultraviolet, excimer laser, electron beam, extreme ultraviolet (EUV), X-ray, and ion beam.

In this case, the content of the acid generating agent in the resist composition is preferably from 0.001% by mass or more to 49% by mass or less based on the total mass of the solid component, more preferably from 1% by mass or more to 40% by mass or less, still more preferably from 3% by mass or more to 30% by mass or less, and particularly preferably from 10% by mass or more to 25% by mass or less. When the resist composition contains the acid generating agent within the above range, a pattern profile with higher sensitivity and lower LFR can be obtained.

In the present embodiment, the acid generation method is not limited as long as an acid is generated within a system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent is not particularly limited and is preferably at least one selected from the group consisting of compounds represented by the following formulas (8-1), (8-2), (8-3), (8-4), (8-5), (8-6), (8-7), and (8-8):

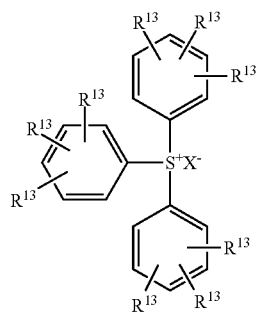

(8-1)

In the formula (8-1), each $R^{13}$ is independently a hydrogen atom, a linear, branched or cyclic alkyl group, a linear, branched or cyclic alkoxy group, a hydroxyl group, or a halogen atom; $X^-$ is an alkyl group, an aryl group, a sulfonic acid ion having a halogen substituted alkyl group or a halogen substituted aryl group, or a halide ion.

The compound represented by the above formula (8-1) is preferably at least one selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, and diphenyl-4-hydroxyphenylsulfonium 10-camphorsulfonate.

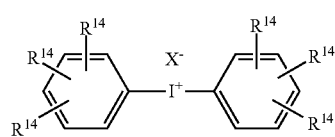

(8-2)

In the formula (8-2), each $R^{14}$ is independently a hydrogen atom, a linear, branched or cyclic alkyl group, a linear, branched or cyclic alkoxy group, a hydroxyl group, or a halogen atom. $X^-$ is as defined in the above formula (8-1).

The compound represented by the above formula (8-2) is preferably at least one selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphersulfonate.

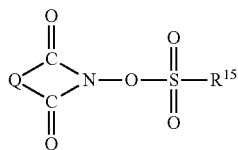
(8-3)

In the formula (8-3), Q is an alkylene group, an arylene group, or an alkoxylene group, and $R^{15}$ is an alkyl group, an aryl group, a halogen substituted alkyl group, or a halogen substituted aryl group.

The compound represented by the above formula (8-3) is preferably at least one selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxyl)bicyclo[2.2.1]hept-5-en-2,3-dicarboxyimide, N-(2-trifluoromethylbenzenesulfonyloxyl)naphthylimide, N-(4-trifluoromethylbenzenesulfonyloxyl)bicyclo[2.2.1]hept-5-en-2,3-dicarboxyimide, N-(4-trifluoromethylbenzenesulfonyloxyl)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxyl)bicyclo[2.2.1]hept-5-en-2,3-dicarboxyimide, N-(1-naphthalenesulfonyloxyl)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

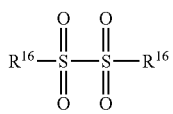
(8-4)

In the formula (8-4), each $R^{16}$ is independently an optionally substituted linear, branched or cyclic alkyl group, an optionally substituted aryl group, an optionally substituted heteroaryl group, or an optionally substituted aralkyl group.

The compound represented by the above formula (8-4) is preferably at least one selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

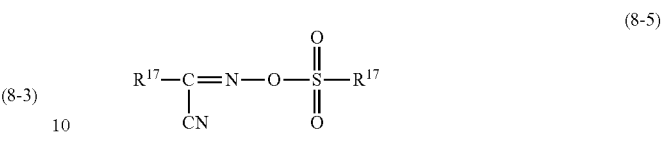
(8-5)

In the formula (8-5), $R^{17}$ may be the same or different, and each $R^{17}$ is independently an optionally substituted linear, branched or cyclic alkyl group, an optionally substituted aryl group, an optionally substituted heteroaryl group, or an optionally substituted aralkyl group.

The compound represented by the above formula (8-5) is preferably at least one selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

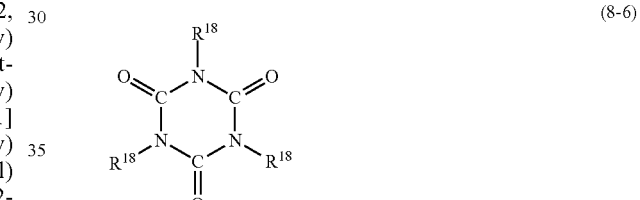
(8-6)

In the formula (8-6), each $R^{18}$ is independently a halogenated alkyl group having one or more chlorine atoms or one or more bromine atoms. The number of carbon atoms of the halogenated alkyl group is preferably 1 to 5.

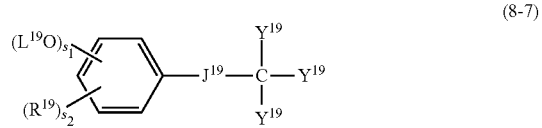
(8-7)

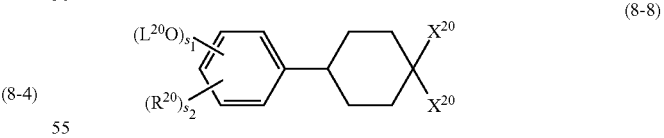
(8-8)

In the formulae (8-7) and (8-8), each $R^{19}$ and $R^{20}$ is independently an alkyl group of C1-3 such as a methyl group, an ethyl group, an n-propyl group, and an isopropyl group; a cycloalkyl group such as a cyclopentyl group and a cyclohexyl group; an alkoxyl group of C1-3 such as a methoxy group, an ethoxy group, and a propoxy group; or an aryl group such as a phenyl group, a toluoyl group, and a naphthyl group, and preferably an aryl group of C6-10. Each $L^{19}$ and $L^{20}$ is independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Among them, particularly, a 1,2-naphthoquinonediazide-4-sulfonyl group and a 1,2-naphthoquinonediazide-5-sulfonyl group are preferable. $s_1$ is an integer of 1 to 3; 52 is an integer of 0 to 4; and $s_1+s_2$ is an integer of 1 to 5. $J^{19}$ is a single bond, a polymethylene group of C1-4, a cycloalkylene group, a phenylene group, a group represented by the following formula (8-7-1), a carbonyl group, an ester group, an amide group, or an ether group. Each $Y^{19}$ is independently a hydrogen atom, an alkyl group (preferably a C1-3 alkyl group), or an aryl group (preferably a C6-10 aryl group), and each $X^{20}$ is independently a group represented by the following formula (8-8-1):

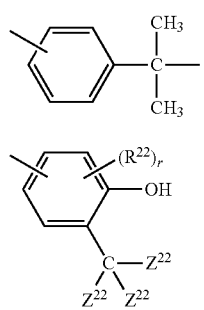

In the formula (8-8-1), each $Z^{22}$ is independently an alkyl group (preferably a C1-3 alkyl group), a cycloalkyl group (preferably a C3-6 cycloalkyl group), or an aryl group (preferably a C6-10 aryl group); each $R^{22}$ is independently an alkyl group (preferably a C1-3 alkyl group), a cycloalkyl group (preferably a C3-6 cycloalkyl group), or an alkoxyl group (preferably a C1-3 alkoxy group); and r is an integer of 0 to 3.

Examples of the other acid generating agent include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the acid generating agents, an acid generating agent having an aromatic ring is preferable, and an acid generating agent represented by the above formula (8-1) or (8-2) is more preferable. An acid generating agent having a sulfonate ion wherein $X^-$ of the above formula (8-1) or (8-2) has an aryl group or a halogen-substituted aryl group is still more preferable; an acid generating agent having a sulfonate ion having an aryl group is particularly preferable; and diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate are particularly preferable. By using the acid generating agent, LER can be further reduced.

The acid generating agent can be used alone or in combination of two or more.

The resist composition of the present embodiment may contain an acid diffusion controlling agent having a function of controlling diffusion of an acid generated from an acid generating agent by radiation irradiation in a resist film to inhibit any unpreferable chemical reaction in an unexposed region or the like. By using such an acid diffusion controlling agent, the storage stability of a resist composition is improved. Also by using the acid diffusion controlling agent, along with improvement of the resolution, the line width change of a resist pattern due to variation in the post exposure delay time before radiation irradiation and the post exposure delay time after radiation irradiation can be inhibited, and the composition has extremely excellent process stability.

Examples of such an acid diffusion controlling agent include, but not particularly limited to, a radiation degradable basic compound such as a nitrogen atom-containing basic compound, a basic sulfonium compound, and a basic iodonium compound. The acid diffusion controlling agent can be used alone or in combination of two or more.

Examples of the above acid diffusion controlling agent include a nitrogen-containing organic compound, and a basic compound degradable by exposure. Examples of the above nitrogen-containing organic compound include a compound represented by the following formula (11).

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms within the same molecule (hereinafter, referred to as a "nitrogen-containing compound (III)"), an amide group-containing compound, a urea compound, and a nitrogen-containing heterocyclic compound. The acid diffusion controlling agent may be used alone as one or may be used in combination of two or more.

In the above formula (11), each $R^{61}$, $R^{62}$, and $R^{63}$ independently represents a hydrogen atom, a linear, branched or cyclic alkyl group, an aryl group, or an aralkyl group independently from each other. The above alkyl group, aryl group, and aralkyl group may be non-substituted or may be substituted with a hydroxyl group or the like. Herein, examples of the above linear, branched or cyclic alkyl group include, but not particularly limited to, the one of C1-15, and preferably C1-10. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the aryl group include the one of C6-12. Specific examples thereof include a phenyl group, a tolyl group, a xylyl group, a cumenyl group, and a 1-naphthyl group. Furthermore, examples of the aralkyl group include, but not particularly limited to, the one of C7-19, and preferably C7-13. Specific examples thereof include a benzyl group, an α-methylbenzyl group, a phenethyl group, and a naphthylmethyl group.

Specific examples of the above nitrogen-containing compound (I) include, but not particularly limited to, mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the above nitrogen-containing compound (II) include, but not particularly limited to, ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 2,2-bis(4-aminophenyl)propane, 2-(3-aminophenyl)-2-(4-aminophenyl)propane, 1,4-bis[1-(4-aminophenyl)-1-methylethyl]benzene, and 1,3-bis[1-(4-aminophenyl)-1-methylethyl]benzene.

Specific examples of the above nitrogen-containing compound (III) include, but not particularly limited to, polymers of polyethyleneimine, polyarylamine, and N-(2-dimethylaminoethyl)acrylamide.

Specific examples of the above amide group-containing compound include, but not particularly limited to, formamide, N-methylformamide, N,N-dimethylformamide, acetamide, N-methylacetamide, N,N-dimethylacetamide, propioneamide, benzamide, pyrrolidone, and N-methylpyrrolidone.

Specific examples of the above urea compound include, but not particularly limited to, urea, methylurea, 1,1-dimethylurea, 1,3-dimethylurea, 1,1,3,3-tetramethylurea, 1,3-diphenylurea, and tri-n-butylthiourea.

Specific examples of the above nitrogen-containing heterocyclic compound include, but not particularly limited to, imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and others such as pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the above radiation degradable basic compound include, but not particularly limited to, a sulfonium compound represented by the following formula (12-1):

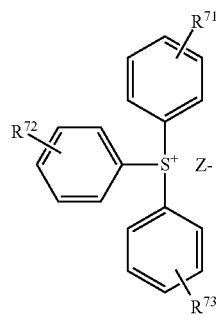
(12-1)

and an iodonium compound represented by the following formula (12-2).

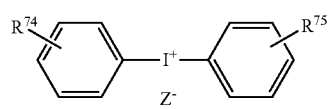
(12-2)

In the above formulae (12-1) and (12-2), each $R^{71}$, $R^{72}$, $R^{73}$, $R^{74}$, and $R^{75}$ independently represents a hydrogen atom, an alkyl group of C1-6, an alkoxyl group of C1-6, a hydroxyl group, or a halogen atom independently from each other. Z-represents $HO^-$, $R-COO^-$ (R represents an alkyl group of C1-6, an aryl group of C6-11, or an alkaryl group of C7-12), or an anion represented by the following formula (12-3).

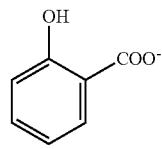
(12-3)

Specific examples of the above radiation degradable basic compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent in the resist composition is preferably from 0.001% by mass or more to 49% by mass or less based on the total mass of the solid component, more preferably from 0.01% by mass or more to 10% by mass or less, still more preferably from 0.01% by mass or more to 5% by mass or less, and particularly preferably from 0.01% by mass or more to 3% by mass or less. When the resist composition contains the acid diffusion controlling agent within the above range, a decrease in resolution, and deterioration of the pattern shape and the dimension fidelity or the like can be further prevented. When the content is within the above range, even though the post exposure delay time from electron beam irradiation to heating after irradiation of radiation becomes longer, deterioration of the shape of the pattern upper layer portion can be prevented. When the content is 10% by mass or less, a decrease in sensitivity, and developability of the unexposed portion or the like can be prevented. Further, by using such an acid diffusion controlling agent, the storage stability of a resist composition is improved, along with improvement of the resolution, the line width change of a resist pattern due to variation in the post exposure delay time before radiation irradiation and the post exposure delay time after radiation irradiation can be inhibited, and the composition has extremely excellent process stability.

To the resist composition of the present embodiment, within the range of not inhibiting the purpose of the present embodiment, if required, as the other solid component, one or two or more of various additive agents such as a dissolution promoting agent, a dissolution controlling agent, a sensitizing agent, a surfactant and an organic carboxylic acid or an oxo acid of phosphor, or derivative thereof can be added.

(Dissolution Promoting Agent)

A dissolution promoting agent is a component having a function of increasing the solubility of a compound represented by the formula (1) or (2) in a developing solution to moderately increase the dissolution rate of the compound upon developing, when the solubility of the compound is low. The dissolution promoting agent can be used, within the range of not deteriorating the effect of the present invention. Examples of the dissolution promoting agent include a low molecular weight phenolic compound. Examples thereof include bisphenols and tris(hydroxyphenyl)methane. These dissolution promoting agents can be used alone or in mixture of two or more. When the resist composition contains the dissolution promoting agent, the content thereof, which is appropriately adjusted according to the kind of the compound represented by the formula (1) or (2) to be used, is preferably more than 0% by mass and 49% by mass or less based on the total mass of the solid component, more preferably more than 0% by mass and 5% by mass or less, still more preferably more than 0% by mass and 1% by mass or less. However, from the viewpoint of not reducing the effect of the present invention, particularly preferably, the dissolution promoting agent is not used.

(Dissolution Controlling Agent)

The dissolution controlling agent is a component having a function of controlling the solubility of the compound represented by the formula (1) or (2) in a developing solution to moderately decrease the dissolution rate of the compound upon developing, when the solubility of the compound is high. As such a dissolution controlling agent, the one which does not chemically change in steps such as calcination of resist coating, radiation irradiation, and development is preferable.

Examples of the dissolution controlling agent include, but not particularly limited to, aromatic hydrocarbons such as phenanthrene, anthracene, and acenaphthene; ketones such as acetophenone, benzophenone, and phenyl naphthyl ketone; and sulfones such as methyl phenyl sulfone, diphenyl sulfone, and dinaphthyl sulfone. These dissolution controlling agents can be used alone or in mixture of two or more.

When the resist composition contains the dissolution controlling agent, the content thereof, which is not particularly limited, is appropriately adjusted according to the kind of the compound represented by the formula (1) or (2) to be used, is preferably more than 0% by mass and 49% by mass or less based on the total mass of the solid component, more preferably more than 0% by mass and 5% by mass or less, still more preferably more than 0% by mass and 1% by mass or less. However, from the viewpoint of not reducing the effect of the present invention, particularly preferably, the dissolution controlling agent is not used.

(Sensitizing Agent)

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent include, but not particularly limited to, benzophenones, biacetyls, pyrenes, phenothiazines, and fluorenes. These sensitizing agents can be used alone or in mixture of two or more. When the resist composition contains the sensitizing agent, the content thereof, which is appropriately adjusted according to the kind of the compound represented by the formula (1) or (2) to be used, is preferably more than 0% by mass and 49% by mass or less based on the total mass of the solid component, more preferably more than 0% by mass and 5% by mass or less, still more preferably more than 0% by mass and 1% by mass or less. However, from the viewpoint of not reducing the effect of the present invention, particularly preferably, the sensitizing agent is not used.

(Surfactant)

The surfactant is a component having a function of improving coatability and striation of the resist composition of the present embodiment, and developability of a resist or the like. Such a surfactant is not particularly limited, and may be any of anionic, cationic, nonionic and amphoteric. A preferable surfactant is a nonionic surfactant. The nonionic surfactant has a good affinity with a solvent used in production of resist compositions and more effects as a surfactant. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). When the resist composition contains the surfactant, the content thereof, which is not particularly limited, is appropriately adjusted according to the kind of the compound represented by the formula (1) or (2) to be used, is preferably more than 0% by mass and 49% by mass or less based on the total mass of the solid component, more preferably more than 0% by mass and 5% by mass or less, still more preferably more than 0% by mass and 1% by mass or less. However, from the viewpoint of not reducing the effect of the present invention, particularly preferably, the surfactant is not used.

(Organic Carboxylic Acid or Oxo Acid of Phosphor or Derivative Thereof)

For the purpose of prevention of sensitivity deterioration or improvement of a resist pattern shape and post exposure delay stability or the like, and as an additional optional component, the resist composition of the present embodiment may contain an organic carboxylic acid or an oxo acid of phosphor or derivative thereof. These components can be used in combination with the acid diffusion controlling agent, or may be used alone. As the organic carboxylic acid, for example, malonic acid, citric acid, malic acid, succinic acid, benzoic acid, and salicylic acid are preferable. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among them, phosphonic acid is particularly preferable.

The organic carboxylic acid or the oxo acid of phosphor or derivative thereof can be used alone or in mixture of two or more. When the resist composition contains the organic carboxylic acid or the oxo acid of phosphor or derivative thereof, the content thereof, which is appropriately adjusted according to the kind of the compound represented by the formula (1) or (2) to be used, is preferably more than 0% by mass and 49% by mass or less based on the total mass of the solid component, more preferably more than 0% by mass and 5% by mass or less, still more preferably more than 0% by mass and 1% by mass or less. However, from the viewpoint of not reducing the effect of the present invention, particularly preferably, the organic carboxylic acid or the oxo acid of phosphor or derivative thereof is not used.

(Other Additive Agent)

Furthermore, the resist composition of the present embodiment can contain one or two or more of additional additive agents other than the dissolution controlling agent, sensitizing agent, surfactant, and organic carboxylic acid or oxo acid of phosphor or derivative thereof, within the range of not inhibiting the purpose of the present invention, if required. Examples of such an additive agent include a dye, a pigment, and an adhesion aid. For example, the resist composition contains the dye or the pigment, and thereby a latent image of the exposed portion can be visualized and influence of halation upon exposure can be alleviated, which is preferable. The resist composition contains the adhesion aid, and thereby adhesiveness to a substrate can be improved, which is preferable. Furthermore, examples of other additive agent include a halation preventing agent, a storage stabilizing agent, a defoaming agent, and a shape improving agent. Specific examples thereof include 4-hydroxy-4'-methylchalkone.

The total content of the additional additive agent is preferably more than 0% by mass and 49% by mass or less based on the total mass of the solid component, more preferably more than 0% by mass and 5% by mass or less, still more preferably more than 0% by mass and 1% by mass or less. However, from the viewpoint of not reducing the effect of the present invention, particularly preferably, the additional additive agent is not used.

The content ratio of the compound represented by the formula (1) and/or the compound represented by the formula (2), the acid generating agent, the acid diffusion controlling agent, and other solid components (F) (compound represented by the formula (1) and/or compound represented by the formula (2)/acid generating agent/acid diffusion controlling agent/other solid components) in the resist composition of the present embodiment is preferably from 50 or more to 99.4 or less/from 0.001 or more to 49 or less/from 0.001 or more to 49 or less/from 0 or more to 49 or less in % by mass based on the solid content (with the total solid content of the resist composition as 100%), more preferably from 55 or more to 90 or less/from 1 or more to 40 or less/from 0.01 or more to 10 or less/from 0 or more to 5 or less, still more preferably from 60 or more to 80 or less/from 3 or more to 30 or less/from 0.01 or more to 5 or less/from 0 or more to 1 or less, and particularly preferably from 60 or more to 70 or less/from 10 or more to 25 or less/from 0.01 or more to 3 or less/0.

The content ratio of each component is selected from each range so that the summation thereof is 100% by mass. The content ratio within the above range makes performance such as sensitivity, resolution, and developability more excellent.

Examples of a method for preparing the resist composition of the present embodiment include, but not particularly limited to, a method of dissolving or dispersing each component in a solvent upon use into a homogenous solution, and then if required, filtering through a filter or the like with a pore diameter of about 0.2 μm, for example.

Examples of the solvent used in the preparation of the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methyl propionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. These solvents can be used alone or in combination of two or more.

The resist composition of the present embodiment can contain one or two or more of resins within the range of not inhibiting the purpose of the present invention. Examples of the resin include, but not particularly limited to, a novolac resin, polyvinyl phenols, polyacrylic acid, polyvinyl alcohol, a styrene-maleic anhydride resin, and a polymer containing acrylic acid, vinyl alcohol or vinylphenol as a monomeric unit, or derivative thereof. In the resist composition, the content of the resin, which is not particularly limited, is appropriately adjusted according to the kind of the compound represented by the formula (1) or (2) to be used, is preferably 30 parts by mass or less based on 100 parts by mass of the compound, more preferably 10 parts by mass or less, and still more preferably 5 parts by mass or less. However, from the viewpoint of not reducing the effect of the present invention, particularly preferably, the resin is not used.

[Resist Pattern Formation Method]

A resist pattern formation method according to the present embodiment is not particularly limited. Suitable examples of the method include a method including steps of coating a substrate with the above resist composition of the present embodiment, thereby forming a resist film, exposing the formed resist film, and developing the exposed resist film to form a resist pattern.

The resist pattern of the present embodiment can be formed as an upper layer resist in a multilayer process.

In order to form a resist pattern, a resist film is formed by coating a conventionally publically known substrate with the above resist composition of the present embodiment using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples include: a wafer of a semiconductor material such as silicon; a substrate made of a metal such as copper, chromium, iron and aluminum; and a glass substrate. Examples of a wiring pattern material include copper, aluminum, nickel, and gold. Also if required, the substrate may be a substrate having an inorganic and/or organic film provided thereon. Examples of the inorganic film include an inorganic antireflection film (inorganic BARC). Examples of the organic film include an organic antireflection film (organic BARC). The above substrate surface treated with hexamethylene disilazane or the like may be used.

Next, the substrate coated with the resist composition is heated if required. The heating conditions can appropriately vary according to the composition of the resist composition, or the like, but are preferably from 20° C. or higher to 250° C. or lower, and more preferably from 20° C. or higher to 150° C. or lower. By heating, the adhesiveness of a resist film to a substrate may be improved, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like can be appropriately selected according to the composition of the resist composition, or the like.

In the present embodiment, in order to stably form a fine pattern with a high degree of accuracy in exposure, the resist film is preferably heated after radiation irradiation. The heating conditions can vary according to the composition of the resist composition, or the like, but are preferably from 20° C. or higher to 250° C. or lower, and more preferably from 20° C. or higher to 150° C. or lower.

Next, by developing the exposed resist film in a developing solution, a predetermined resist pattern is formed.

As the developing solution, a solvent having a solubility parameter (SP value) close to that of the compound represented by the formula (1) or (2) to be used is preferably contained. Examples of the solvent contained in the developing solution include: polar solvents such as a ketone-based solvent, an ester-based solvent, an alcohol-based solvent, an amide-based solvent, and an ether-based solvent; organic solvents such as a hydrocarbon-based solvent; and an alkaline aqueous solution.

Depending on the kind of the developing solution, a positive type resist pattern or a negative type resist pattern can be selectively prepared. In general, when the developing solution contains a polar solvent such as a ketone-based solvent, an ester-based solvent, an alcohol-based solvent, an amide-based solvent, and an ether-based solvent, and a hydrocarbon-based solvent, a negative type resist pattern is obtained. When the developing solution contains an alkaline aqueous solution, a positive type resist pattern is obtained.

Examples of the ketone-based solvent include, but not particularly limited to, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include, but not particularly limited to, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include, but not particularly limited to, an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include, but not particularly limited to, dioxane and tetrahydrofuran in addition to the glycol ether-based solvents.

Examples of the amide-based solvent include, but not particularly limited to, N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include, but not particularly limited to, an aromatic hydrocarbon-based solvent such as toluene and xylene; and an aliphatic hydrocarbon-based solvent such as pentane, hexane, octane, and decane.

The above organic solvents can be used alone or in combination of two or more. One or two or more of the organic solvents may be used in combination with a solvent other than those described above or water within the range of not inhibiting the performance as a solvent. However, in order to more effectively and reliably exhibit the effect of the present invention, the water content ratio as the whole developing solution is preferably less than 70% by mass, more preferably less than 50% by mass, still more preferably less than 30% by mass, and particularly preferably less than 10% by mass. Particularly preferably, the developing solution is substantially moisture free. That is, the content of the organic solvent in the developing solution is not particularly limited, but is preferably from 30% by mass or more to 100% by mass or less based on the total amount of the developing solution, more preferably from 50% by mass or more to 100% by mass or less, still more preferably from 70% by mass or more to 100% by mass or less, yet still more preferably from 90% by mass or more to 100% by mass or less, and particularly preferably from 95% by mass or more to 100% by mass or less.

Examples of the alkaline aqueous solution include, but not particularly limited to, an aqueous solution of an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one of solvent selected from the group consisting of a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and still more preferably 2 kPa or less. The evaporation of the developing solution on the substrate or in a developing cup is inhibited by setting the vapor pressure of the developing solution to 5 kPa or less, to improve temperature uniformity within a substrate surface, thereby resulting in improvement in size uniformity within the substrate surface.

For setting the vapor pressure of the developing solution to 5 kPa or less at 20° C., a solvent having such a vapor pressure can be contained in the developing solution. Specific examples of the solvent having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples of a solvent having a vapor pressure of 2 kPa or less which is a still more preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required.

Examples of such a surfactant include, but not particularly limited to, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is more preferably used.

The amount of the surfactant added to the developing solution is, normally, preferably from 0.001% by mass or more to 5% by mass or less based on the total amount of the developing solution, more preferably from 0.005% by mass or more to 2% by mass or less, and still more preferably from 0.01% by mass or more to 0.5% by mass or less.

Examples of the development method include a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method). The developing time is not particularly limited, but is preferably 10 seconds to 90 seconds.

In the present embodiment, after the step of conducting development, a step of stopping the development by the replacement of the developing solution with another solvent may be provided.

In the present embodiment, after the step of conducting development, a step of rinsing the substrate and the resist pattern formed thereon with a rinsing solution containing an organic solvent (hereinafter, may be referred to as a "rinsing step") is preferably provided.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, a rinsing solution containing at least one of organic solvent selected from the group consisting of a hydrocarbon-based solvent, a ketone-based solvent, an ester-based solvent, an alcohol-based solvent, an amide-based solvent, and an ether-based solvent is preferably used.

More preferably, the rinsing solution used in the rinsing step contains at least one of organic solvent selected from the group consisting of a ketone-based solvent, an ester-based solvent, an alcohol-based solvent and an amide-based solvent. Still more preferably, the rinsing solution used in the rinsing step contains an alcohol-based solvent and/or an ester-based solvent. Yet still more preferably, the rinsing solution used in the rinsing step contains a monohydric alcohol. Particularly preferably, the rinsing solution used in the rinsing step contains a monohydric alcohol having C5 or more. The time required for rinsing step is not particularly limited, but is preferably 10 seconds to 90 seconds.

Herein, examples of the monohydric alcohol used in the rinsing step after development include a linear, branched or cyclic monohydric alcohol. Specific examples include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol. Examples of particularly preferable monohydric alcohol having C5 or more include 1-hexanol, 2-hexanol, 4-methyl-2-pentanol, 1-pentanol, and 3-methyl-1-butanol.

The rinsing solution may contain one or two or more of above each component and may further contain an organic solvent other than those described above.

The water content ratio in the rinsing solution is not particularly limited, but is preferably 10% by mass or less, more preferably 5% by mass or less, and still more preferably 3% by mass or less. By setting the water content ratio to 10% by mass or less, better development characteristics can be obtained.

The vapor pressure at 20° C. of the rinsing solution used after development is preferably from 0.05 kPa or more to 5 kPa or less, more preferably from 0.1 kPa or more to 5 kPa or less, and still more preferably from 0.12 kPa or more to 3 kPa or less. By setting the vapor pressure of the rinsing solution to from 0.05 kPa or more to 5 kPa or less, the temperature uniformity in the substrate surface is enhanced and moreover, swelling due to permeation of the rinsing solution is further inhibited. As a result, the dimensional uniformity in the substrate surface is further improved.

The rinsing solution may also contain an appropriate amount of a surfactant.

In the rinsing step, the substrate after development is rinsed using the organic solvent-containing rinsing solution. Examples of the method for rinsing treatment include, but not particularly limited to, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method). Among them, the spin coating method is preferable, and it is preferable to conduct rinsing by the spin coating method and then spin the substrate at a rotational speed of 2,000 rpm to 4,000 rpm, to remove the rinsing solution from the substrate surface.

After forming the resist pattern, a pattern wiring board is obtained by etching. As the etching method, a publicly known method such as dry etching using plasma gas, and wet etching with an alkaline solution, a copper (II) chloride solution, and an iron (III) chloride solution or the like can be adopted.

After forming the resist pattern, plating can also be conducted. Examples of the plating method include copper plating, solder plating, nickel plating, and gold plating.

The remaining resist pattern after etching can be peeled by an organic solvent. Examples of the above organic solvent include PGMEA (propylene glycol monomethyl ether acetate), PGME (propylene glycol monomethyl ether), and EL (ethyl lactate). Examples of the peeling method include a dipping method and a spraying method. A wiring board having a resist pattern formed thereon may be a multilayer wiring board, and may have a small diameter through hole.

The wiring board obtained in the present embodiment can also be formed by a method for forming a resist pattern, then depositing a metal in vacuum, and subsequently dissolving the resist pattern in a solution, i.e., a liftoff method.

[Polyphenol Derivative]

The polyphenol derivative of the present embodiment is a compound represented by the following formula (3) or a polyphenol derivative represented by the following formula (4).

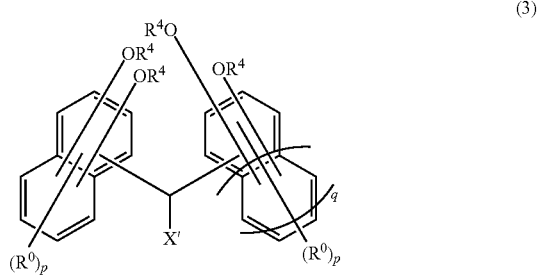

(3)

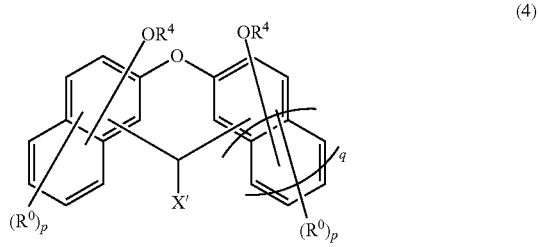

(4)

In the formulae (3) and (4), each X' is independently a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; $R^4$ is as defined in the above formula (1-1); each p is independently an integer of 0 to 5; and q is 0 or 1.

The compound represented by the above formula (3) and the polyphenol derivative represented by the above formula (4) are preferably a compound represented by the following formula (3-1) and a compound represented by the following formula (4-1), respectively:

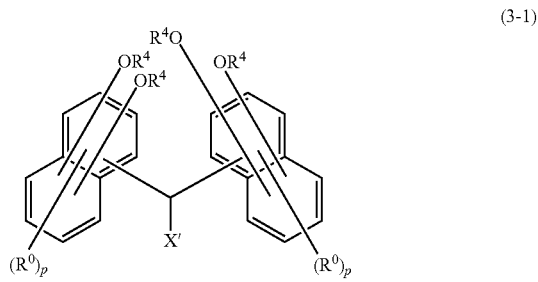

(3-1)

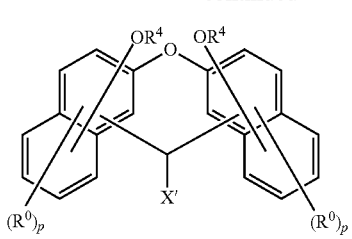

(4-1)

In the formulae (3-1) and (4-1), each X' is independently a hydrogen atom or a C1-18 monovalent substituent; each $R^0$ is independently a C1-4 alkyl group or a halogen atom and may be the same as or different from each other on the same naphthalene ring; $R^4$ is as defined in the above formula (1-1); and each p is independently an integer of 0 to 5.

The polyphenol derivative of the present embodiment has a naphthalene skeleton and is thereby excellent in heat resistance. The polyphenol derivative exhibits an effect of being also excellent in solubility in a safe solvent in addition to heat resistance.

The position of —$OR^4$ on the naphthalene ring is not particularly limited and is preferably position 1,5, 1,6, 1,7, 2,3, 2,7, or 2,6 in terms of industrial usability of raw materials, and more preferably position 2,6 in terms of higher solubility in a safe solvent and low crystallinity.

EXAMPLES

The present embodiment will be more specifically described with reference to examples below. However, the present invention is not limited to these examples.

Hereinafter, a method for measuring a compound in examples and a method for evaluating resist performance or the like are shown.

[Measurement Method]

(1) Structure of Compound

The structure of a compound was confirmed using a measurement apparatus Advance600II spectrometer (product name) manufactured by Bruker Corporation according to $^1$H-NMR measurement under the following conditions:

Frequency: 400 MHz

Solvent: d6-DMSO (except for Synthesis Example 4)

Internal standard: TMS

Measurement temperature: 23° C.

(2) Molecular Weight of Compound

A compound was measured using an analysis apparatus Agilent 5975/6890N (product name) manufactured by Agilent Corporation according to GC-MS analysis or measured using an analysis apparatus Acquity UPLC/MALDI-Synapt HDMS (product name) manufactured by Water Corporation according to LC-MS analysis.

(3) Dissolution Rate of Amorphous Film (Before and after Exposure) in Developing Solution An amorphous film was dipped in a developing solution at 23° C. for a predetermined time, and film thicknesses before and after dipping were visually confirmed to determine a dissolution rate.

[Evaluation Method]

(1) Solubility Test of Compound in Safe Solvent

The solubility of the compound in CHN, PGME and PGMEA was evaluated according to the following standard using the dissolution amount in each solvent. The dissolution amount was determined by precisely weighing the compound in a test tube at 23° C.; adding the target solvent to the compound so that a predetermined concentration of the liquid to be obtained was set; applying a ultrasonic wave to the liquid in an ultrasonic washing machine for 30 minutes; and visually evaluating the state of the resulting liquid.

A: 5.0% by mass Dissolution amount

B: 3.0% by mass Dissolution amount <5.0% by mass

C: Dissolution amount <3.0% by mass (2) Heat Resistance

Each prepared resist composition was evaluated for its heat resistance by the following procedures.

A clean silicon wafer was spin coated with a resist, and then heated (baked) in an oven of 110° C. to form a resist film with a thickness of 60 nm. The film was visually observed. A good film having no defect was judged as having good heat resistance and evaluated as "◯". A film found to have defect was judged as not having good heat resistance and evaluated as "x".

(3) Pattern Evaluation of Resist Pattern (Resolution, Shape, LER)

The line and space of each resist pattern was observed by a scanning electron microscope (S-4800 (product name) manufactured by Hitachi High-Technologies Corporation). The pattern having the resolution of 30 nm was evaluated for whether or not pattern shape, line edge roughness, and sensitivity were good.

The rectangular pattern shape was judged as being good. For LER (line edge roughness), the distance between the edge and the standard line was measured using a Terminal PC V5 Offline Length Measuring Software (manufactured by Hitachi Science Systems) adaptable to SEM for Semiconductor (manufactured by Hitachi High-Technologies Corporation) for arbitrary 300 points in the length direction (0.75 μm) with 50 nm interval and 1:1 line and space to calculate the standard deviation (3σ). The standard deviation of less than 5 nm was judged as being good. The minimum line width of the pattern which could be well formed was used as the resolution of the pattern. The minimum dose amount (μC/cm$^2$) when the pattern could be well formed was used as sensitivity. The sensitivity of less than 150 μC/cm$^2$ was judged as being good.

A resist pattern having good pattern shape, LER, and sensitivity was evaluated as "◯" (good). Other cases were evaluated as "x" (poor).

Synthesis Examples (Synthesis Example 1) Synthesis of BisN-1

In a container (internal capacity: 100 mL) equipped with a stirrer, a condenser tube, and a burette, after injecting 30 mL of methyl isobutyl ketone, 3.20 g (20 mmol) of 2,6-naphthalenediol (reagent manufactured by Sigma-Aldrich Corporation) and 1.82 g (10 mmol) of 4-biphenylcarboxaldehyde (manufactured by Mitsubishi Gas Chemical Company, Inc.) were charged thereto, and 5 mL of 95% sulfuric acid was further added thereto. The obtained reaction solution was stirred at 30° C. for 6 hours such that the reaction was allowed to proceed. Next, the solution after the reaction was concentrated. The reaction product was precipitated by the addition of 50 g of pure water. After cooling to room temperature, the precipitates were separated by filtration.

The obtained solid was further filtered, dried, and then separated and purified by column chromatography to obtain 0.2 g of the objective compound (BisN-1) represented by the following formula.

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.5 (17H, Ph-H), 6.8 (1H, C—H)

The signals of protons at positions 3 and 4 were found as a doublet, thereby confirming that the substitution position of 2,6-naphthalenediol was position 1.

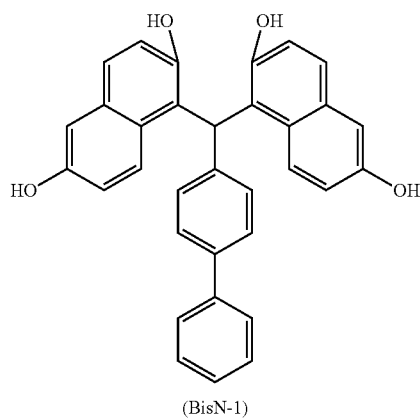 [SMILES: Oc1ccc2c(C(c3ccc(-c4ccccc4)cc3)c3c(O)ccc4cc(O)ccc34)c(O)ccc2c1]

(BisN-1)

Synthesis Examples (Synthesis Example 1) Synthesis of BisN-1-BOC

In a container (internal capacity: 200 mL) equipped with a stirrer, a condenser tube, and a burette, after injecting 100 mL of acetone, 6.1 g (12.5 mmol) of BisN-1 and 11.0 g (50 mmol) of di-t-butyl dicarbonate (manufactured by Sigma-Aldrich Corporation) were charged thereto, and 6.9 g (50 mmol) of potassium carbonate (manufactured by Sigma-Aldrich Corporation) were added thereto. The obtained reaction solution was stirred for 6 hours at 20° C. such that the reaction was allowed to proceed. Next, the solution after the reaction was concentrated. The reaction product was precipitated by the addition of 100 g of pure water. After cooling to room temperature, the precipitates were separated by filtration.

The obtained solid was further filtered, dried, and then separated and purified by column chromatography to obtain 2.0 g of the objective compound (BisN-1-BOC) represented by the following formula.

As a result of measuring the molecular weight of the obtained compound by the above method, it was 884.

The obtained compound was subjected to NMR measurement under the above measurement conditions. The following peaks were found, and the compound was confirmed to have a chemical structure of the following formula.

δ (ppm) 7.2-8.7 (17H, Ph-H), 6.7 (1H, C—H), 1.6 (36H, C—C$\underline{H}_3$)

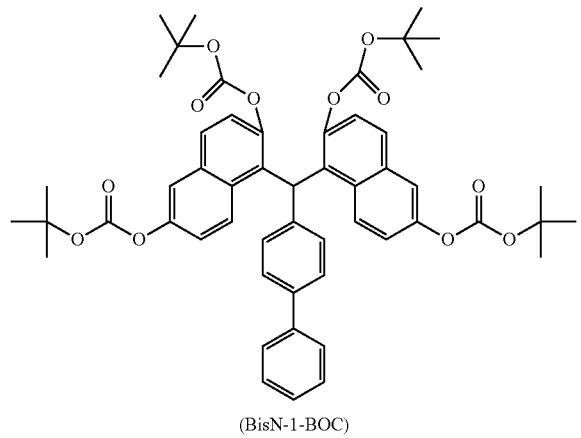 [SMILES: CC(C)(C)OC(=O)Oc1ccc2c(C(c3ccc(-c4ccccc4)cc3)c3c(OC(=O)OC(C)(C)C)ccc4cc(OC(=O)OC(C)(C)C)ccc34)c(OC(=O)OC(C)(C)C)ccc2c1]

(BisN-1-BOC)

The solubility in a safe solvent was evaluated by the above method. The results are shown in Example 1 of Table 1.

(Synthesis Example 2) Synthesis of BisN-1-MeBOC

In a container (internal capacity: 200 mL) equipped with a stirrer, a condenser tube, and a burette, after injecting 100 mL of acetone, 5.8 g (12.4 mmol) of BisN-1 and 10.8 g (54 mmol) of t-butyl bromoacetate (manufactured by Sigma-Aldrich Corporation) were charged thereto, and 7.6 g (54 mmol) of potassium carbonate (manufactured by Sigma-Aldrich Corporation) and 1.6 g of 18-crown-6 were further added thereto. The obtained reaction solution was stirred for 3 hours under reflux such that the reaction was allowed to proceed. Next, the solution after the reaction was concentrated. The reaction product was precipitated by the addition of 100 g of pure water. After cooling to room temperature, the precipitates were separated by filtration.

The obtained solid was further filtered, dried, and then separated and purified by column chromatography to obtain 1.5 g of the objective compound (BisN-1-MeBOC) represented by the following formula.

As a result of measuring the molecular weight of the obtained compound by the above method, it was 940.

The obtained compound was subjected to NMR measurement under the above measurement conditions. The following peaks were found, and the compound was confirmed to have a chemical structure of the following formula.

δ (ppm) 7.2-8.7 (17H, Ph-H), 6.7 (1H, C—H), 4.7-4.8 (8H, C—C$\underline{H}_2$—C), 1.3-1.4 (36H, C—C$\underline{H}_3$)

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.5 (19H, Ph-H), 6.8 (1H, C—H)

The signals of protons at positions 3 and 4 were found as a doublet, thereby confirming that the substitution position of 2,6-naphthalenediol was position 1.

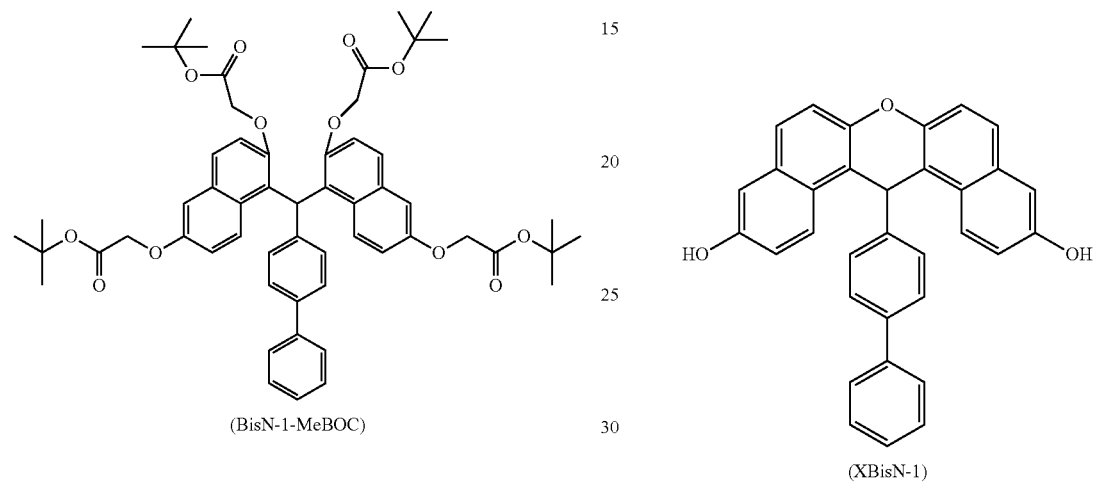

(BisN-1-MeBOC)

(XBisN-1)

The solubility in a safe solvent was evaluated by the above method. The results are shown in Example 2 of Table 1.

(Synthesis Example 2) Synthesis of XBisN-1

In a container (internal capacity: 100 mL) equipped with a stirrer, a condenser tube, and a burette, after injecting 30 mL of methyl isobutyl ketone, 3.20 g (20 mmol) of 2,6-naphthalenediol (reagent manufactured by Sigma-Aldrich Corporation) and 1.82 g (10 mmol) of 4-biphenylcarboxaldehyde (manufactured by Mitsubishi Gas Chemical Company, Inc.) were charged thereto, and 5 mL of 95% sulfuric acid was further added thereto. The obtained reaction solution was stirred at 30° C. for 6 hours such that the reaction was allowed to proceed. Next, the solution after the reaction was concentrated. The reaction product was precipitated by the addition of 50 g of pure water. After cooling to room temperature, the precipitates were separated by filtration.

The obtained solid was further filtered, dried, and then separated and purified by column chromatography to obtain 0.2 g of the objective compound (XBisN-1) represented by the following formula.

As a result of measuring the molecular weight of the obtained compound by the above method, it was 466.

(Synthesis Example 3) Synthesis of XBisN-1-BOC

In a container (internal capacity: 200 mL) equipped with a stirrer, a condenser tube, and a burette, after injecting 100 mL of acetone, 5.8 g (12.5 mmol) of XBisN-1 and 5.5 g (25 mmol) of di-t-butyl dicarbonate (manufactured by Sigma-Aldrich Corporation) were charged thereto, and 3.45 g (25 mmol) of potassium carbonate (manufactured by Sigma-Aldrich Corporation) were added thereto. The obtained reaction solution was stirred for 6 hours at 20° C. such that the reaction was allowed to proceed. Next, the solution after the reaction was concentrated. The reaction product was precipitated by the addition of 100 g of pure water. After cooling to room temperature, the precipitates were separated by filtration.

The obtained solid was further filtered, dried, and then separated and purified by column chromatography to obtain 2.0 g of the objective compound (XBisN-1-BOC) represented by the following formula.

As a result of measuring the molecular weight of the obtained compound by the above method, it was 666.

The obtained compound was subjected to NMR measurement under the above measurement conditions. The following peaks were found, and the compound was confirmed to have a chemical structure of the following formula.

δ (ppm) 7.2-8.7 (19H, Ph-H), 6.8 (1H, C—H), 1.6 (18H, C—CH₃)

δ (ppm) 7.2-8.7 (19H, Ph-H), 6.7 (1H, C—H), 4.7-4.8 (4H, C—CH₂—C), 1.3-1.4 (18H, C—CH₃)

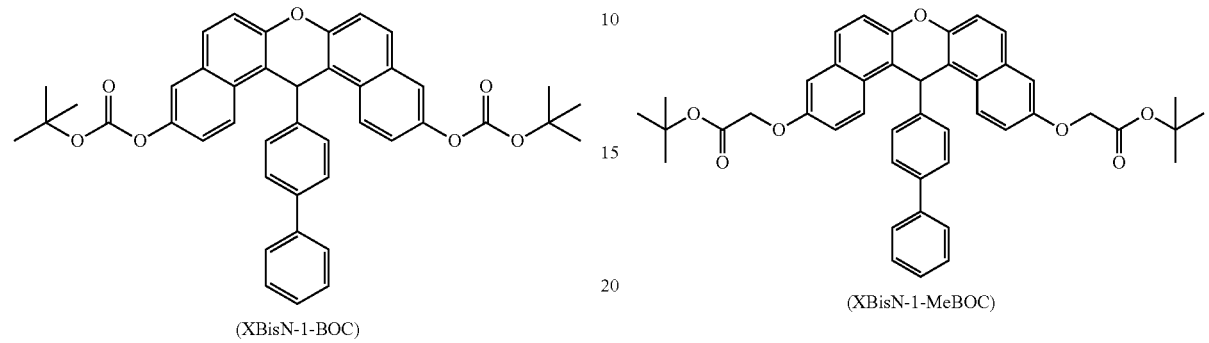

(XBisN-1-BOC)

(XBisN-1-MeBOC)

The solubility in a safe solvent was evaluated by the above method. The results are shown in Example 3 of Table 1.

(Synthesis Example 4) Synthesis of XBisN-1-MeBOC

In a container (internal capacity: 200 mL) equipped with a stirrer, a condenser tube, and a burette, after injecting 100 mL of acetone, 5.8 g (12.4 mmol) of XBisN-1 and 5.4 g (27 mmol) of t-butyl bromoacetate (manufactured by Sigma-Aldrich Corporation) were charged thereto, and 3.8 g (27 mmol) of potassium carbonate (manufactured by Sigma-Aldrich Corporation) and 0.8 g of 18-crown-6 were further added thereto. The obtained reaction solution was stirred for 3 hours under reflux such that the reaction was allowed to proceed. Next, the solution after the reaction was concentrated. The reaction product was precipitated by the addition of 100 g of pure water. After cooling to room temperature, the precipitates were separated by filtration.

The obtained solid was further filtered, dried, and then separated and purified by column chromatography to obtain 1.8 g of the objective compound (XBisN-1-MeBOC) represented by the following formula.

As a result of measuring the molecular weight of the obtained compound by the above method, it was 694.

The obtained compound was subjected to NMR measurement under the above measurement conditions. The following peaks were found, and the compound was confirmed to have a chemical structure of the following formula.

The solubility in a safe solvent was evaluated by the above method. The results are shown in Example 4 of Table 1.

(Synthesis Comparative Example 1) Synthesis of TetP-1 (Polyphenol Derivative)

In a four necked flask (1000 mL) sufficiently dried, substituted with nitrogen, and equipped with a dropping funnel, a Dimroth condenser tube, a thermometer, and a stirring blade, 108.8 g (0.8 mol) of 2,3,6-trimethylphenol manufactured by Honshu Chemical Industry Co., Ltd. and 18.4 g (0.1 mol) of 2,7-naphthalenedicarboxaldehyde manufactured by Mitsubishi Gas Chemical Company, Inc. were charged and mixed under a nitrogen gas stream, and dissolved by heating to about 60° C. 0.1 mL of sulfuric acid, 0.8 mL of 3-mercaptopropionic acid, and 10 mL of toluene were added thereto, and the mixture was stirred such that the reaction was allowed to proceed.

The solution after the reaction was stood to cool, and after it reached room temperature, it was cooled in an ice bath. It was left at rest for 1 hour, to produce a target light yellow crude crystal, which was filtered. The filtered crude crystal was washed with warm water of 60° C. by stirring and recrystallized to obtain 8.99 g of the objective product (TetP-1) represented by the following formula. Subsequently, 2.50 g of the objective compound (TetP-1-BOC) represented by the following formula was obtained by reacting TetP-1 with di-t-butyl dicarbonate in the same way as in Synthesis Example 1 except that TetP-1 was used instead of BisN-1.

The obtained compound was subjected to NMR measurement under the above measurement conditions. The compound was confirmed to have a chemical structure of the following formula.

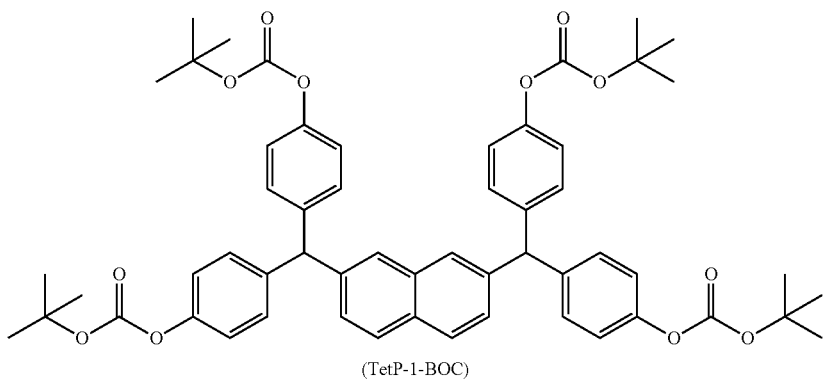 [SMILES: CC(C)(C)OC(=O)Oc1ccc(C(c2ccc(OC(=O)OC(C)(C)C)cc2)c2ccc3ccc(C(c4ccc(OC(=O)OC(C)(C)C)cc4)c4ccc(OC(=O)OC(C)(C)C)cc4)cc3c2)cc1]

(TetP-1-BOC)

The solubility in a safe solvent was evaluated by the above method. The results are shown in Comparative Example 1 of Table 1.

(Synthesis Comparative Example 2) Synthesis of CR-1 (Polyphenol Derivative)

74.3 g (3.71 mol) of anhydrous HF and 50.5 g (0.744 mol) of $BF_3$ were charged into a temperature-controllable autoclave (made of SUS316L) having an internal capacity of 500 mL and equipped with an electromagnetic stirring device, and the content was stirred and increased in pressure with carbon monoxide to 2 MPa while maintaining the liquid temperature to −30° C. Thereafter, while maintaining the pressure to 2 MPa and the liquid temperature to −30° C., a raw material obtained by mixing 57.0 g (0.248 mol) of 4-cyclohexylbenzene and 50.0 g of n-heptane was fed thereto, and maintained the content for 1 hour. Subsequently, the content was collected into ice, diluted with benzene, and neutralized to provide an oily layer, which was analyzed by gas chromatograph for evaluating the reaction performance. The 4-cyclohexylbenzene conversion was 100%, and the 4-cyclohexylbenzaldehyde selectivity was 97.3%.

The target component was isolated by simple distillation and analyzed by GC-MS, and the result exhibited a molecular weight of 188, which was 4-cyclohexylbenzaldehyde (CHBAL) represented by the following formula. The obtained compound was subjected to NMR measurement under the above measurement conditions and thereby confirmed to have a chemical structure of the following formula.

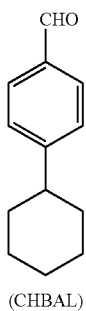

(CHBAL)

Under a nitrogen gas stream, resorcinol manufactured by Kanto Chemical Co., Inc. (22 g, 0.2 mol), the above CHBAL (46.0 g, 0.2 mol), and dehydrated ethanol (200 mL) were charged to a four necked flask (1000 mL) sufficiently dried, substituted with nitrogen, and equipped with a dropping funnel, a Dimroth condenser tube, a thermometer, and a stirring blade, to prepare an ethanol solution. This solution was heated to 85° C. by a mantle heater while stirring. Then, 75 mL of concentrated hydrochloric acid (35%) was dropped thereto through the dropping funnel for 30 minutes, and continuously stirred at 85° C. for 3 hours such that the reaction was allowed to proceed. The solution after the reaction was stood to cool, and after it reached room temperature, it was cooled in an ice bath. It was left at rest for 1 hour, to produce a target light yellow crude crystal, which was filtered. The filtered crude crystal was washed twice with 500 mL of methanol, filtered, and dried in a vacuum to obtain 50 g of the product (CR-1) represented by the following formula. Subsequently, 25 g of the objective compound (CR-1-BOC) represented by the following formula was obtained by reacting CR-1 with di-t-butyl dicarbonate in the same way as in Synthesis Example 1 except that CR-1 was used instead of BisN-1.

The obtained compound was subjected to NMR measurement under the above measurement conditions. The compound was confirmed to have a chemical structure of the following formula.

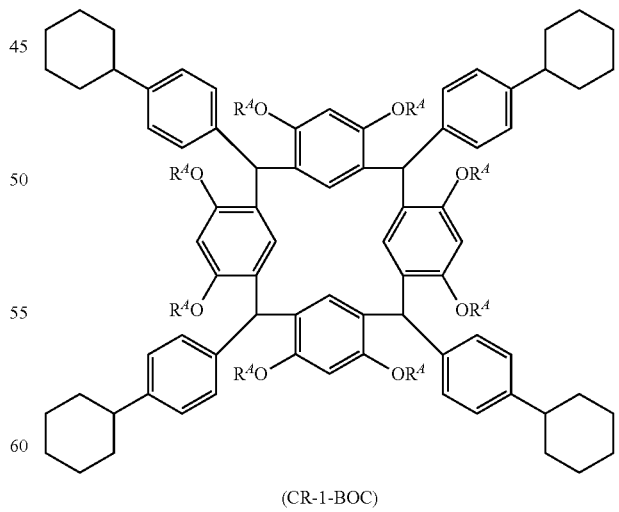

(CR-1-BOC)

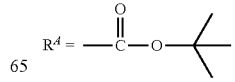

The solubility in a safe solvent was evaluated by the above method. The results are shown in Comparative Example 2 of Table 1.

Examples and Comparative Examples

Synthesis of Resist Composition

Examples 1 to 4 and Comparative Examples 1 and 2

Resist compositions having formulations shown in Table 1 were prepared using the polyphenol derivatives synthesized above. Of the components of the resist composition in Table 1, as the acid generating agent, the acid diffusion controlling agent, and the solvent, the followings were used:
Acid Generating Agent (P-1): triphenylbenzenesulfonium trifluoromethanesulfonate (manufactured by Midori Kagaku Co., Ltd.)
Acid Diffusion Controlling Agent (Q-1): trioctylamine (manufactured by Tokyo Kasei Kogyo Co., Ltd.)
Solvent (S-1): propylene glycol monomethyl ether (manufactured by Tokyo Kasei Kogyo Co., Ltd.)

The heat resistance of the obtained compositions was evaluated by the above method. The obtained results are shown in Table 1.

Resist patterns were formed using the obtained resist compositions according to the following procedures. First, a clean silicon wafer was spin coated with a resist composition, and then heated before exposure (prebaked: PB) in an oven of 110° C. to form a resist film with a thickness of 60 nm. The obtained resist film was irradiated with electron beams of 1:1 line and space setting with a 50 nm interval, a 40 nm interval, and a 30 nm interval using an electron beam lithography system (product name "ELS-7500" manufactured by ELIONIX INC.). After irradiation, it was heated at each predetermined temperature for 90 seconds, and immersed in 2.38% by mass TMAH alkaline developing solution for 60 seconds for development. Subsequently, it was washed by rinsing with ultrapure water, and dried to form a positive type resist pattern.

Pattern evaluation was carried out for the obtained resist patterns according to the above method. The obtained results are shown in Table 1.

Negative type resist patterns were formed using the obtained resist compositions in the same way as above except that: the developing solution was changed from 2.38% by mass TMAH alkaline developing solution to butyl acetate; the developing time was changed such that the development was continued until the pattern could be developed; and the rinsing was not conducted.

Pattern evaluation was carried out for the obtained resist patterns according to the above method. The obtained results are shown in Table 1.

As is evident from Table 1, the resists of Examples 1 to 4 and Comparative Example 2 were confirmed to be good films having no defect and have good heat resistance. On the other hand, the resist of Comparative Example 1 was confirmed to be a poor film having many defects and have poor heat resistance.

As is evident from Table 1, in the resists of Examples 1 to 4, resist patterns with good resolution of 30 nm and good sensitivity could be obtained. The roughness of the patterns was also small, and their shapes were also good. On the other hand, in the resists of Comparative Example 1 and 2, none of resist patterns with resolution of 40 nm or 30 nm could be obtained.

TABLE 1

| | Polyphenol derivative | Solubility test of compound in safe solvent | | |
|---|---|---|---|---|
| | | CHN | PGME | PGMEA |
| Example 1 | BisN-1-BOC | A | B | A |
| Example 2 | BisN-1-MeBOC | A | A | B |
| Example 3 | XBisN-1-BOC | A | B | A |
| Example 4 | XBisN-1-MeBOC | A | A | B |
| Comparative Example 1 | TetP-1-BOC | A | A | A |
| Comparative Example 2 | CR-1-BOC | B | B | C |

| | Resist composition | | | | Resist pattern evaluation | | |
|---|---|---|---|---|---|---|---|
| | Polyphenol derivative [g] | Acid generating agent (C) P-1 [g] | Acid diffusion controlling agent (E) Q-1 [g] | Solvent S-1 [g] | Heat resistance evaluation | Pattern evaluation TMAH development | Pattern evaluation butyl acetate development |
| Example 1 | 1.0 | 0.3 | 0.03 | 50.0 | ○ | ○ | ○ |
| Example 2 | 1.0 | 0.3 | 0.03 | 50.0 | ○ | ○ | ○ |
| Example 3 | 1.0 | 0.3 | 0.03 | 50.0 | ○ | ○ | ○ |
| Example 4 | 1.0 | 0.3 | 0.03 | 50.0 | ○ | ○ | ○ |
| Comparative Example 1 | 1.0 | 0.3 | 0.03 | 50.0 | x | x | x |
| Comparative Example 2 | 1.0 | 0.3 | 0.03 | 50.0 | ○ | x | x |

The above results demonstrated that the resist composition containing the compound according to the present invention has higher sensitivity than that of the composition containing TetP-1 or CR-1, and enables the formation of the resist pattern having a better shape having smaller roughness. As long as the requirements of the above present invention are met, compounds other than those described in examples also exhibit the same effects.

This application is based on Japanese Patent Application No. 2013-23641 filed on Feb. 8, 2013, the entire contents of which are hereby incorporated by reference.

The present invention can provide a resist composition which is excellent in heat resistance, has high solubility in a safe solvent, has high sensitivity, and can impart a good shape to a resist pattern, and a method for forming a resist pattern using the composition. Thus, the resist composition of the present invention is useful in the fields of semiconductors, displays, photomasks, thin film magnetic heads, compound semiconductors, and research and development, or the like in which resist compositions such as acid amplification type non-polymer based resist materials are used.

The present invention can also provide a polyphenol derivative which is excellent in heat resistance and has high solubility in a safe solvent. Thus, the polyphenol compound of the present invention is preferably used in base materials for photosensitive materials such as photoresists for semiconductors, raw materials for epoxy resins or curing agents used in sealing materials or the like of integrated circuits, developers or discoloration preventing agents used in thermal recording materials, and other additives such as germicides and antifungal and antibacterial agents, and the like.

The invention claimed is:

1. A resist composition comprising:
   a compound represented by the following formula (1) or (2):

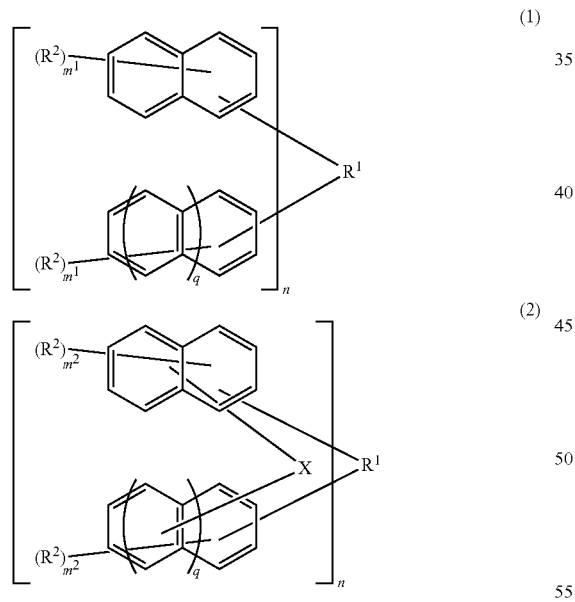

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^2$ is independently a hydrogen atom, a halogen atom, a linear, branched, or cyclic alkyl group of 1 to 10 carbon atoms, an aryl group of 6 to 10 carbon atoms, an alkenyl group of 2 to 10 carbon atoms, a hydroxyl group, or a group in which a hydrogen atom of a hydroxyl group is substituted with an acid dissociation group, and may be the same as or different from each other on the same naphthalene ring or benzene ring; at least one of $R^2$ is a group in which a hydrogen atom of a hydroxyl group is substituted with an acid dissociation group; n is an integer of 1 to 4; structural formulas of repeating units in the formulas (1) and (2) may be the same as or different from each other; in the formula (1), each $m^1$ is independently an integer of 1 to 7; and in the formula (2), each X is independently an oxygen atom or a sulfur atom, each $m^2$ is independently an integer of 1 to 6, and each q is 1; wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group; and an acid generating agent, wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1),

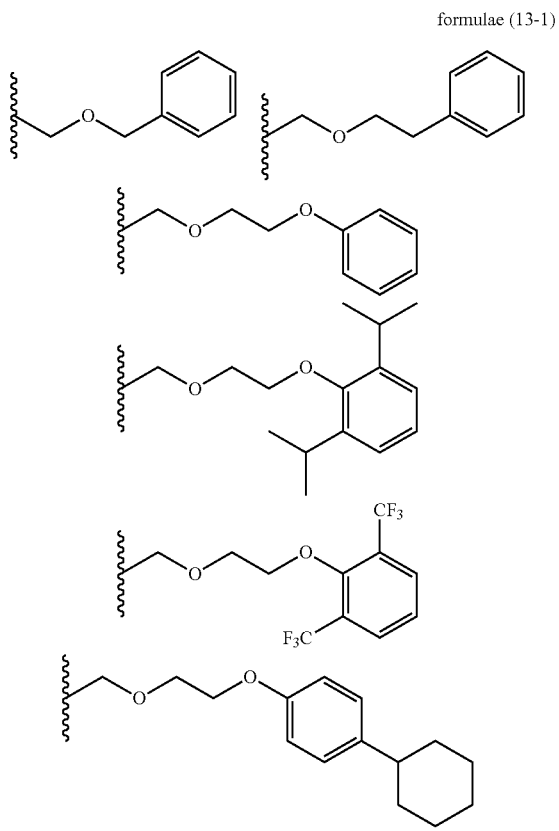

formulae (13-1)

-continued

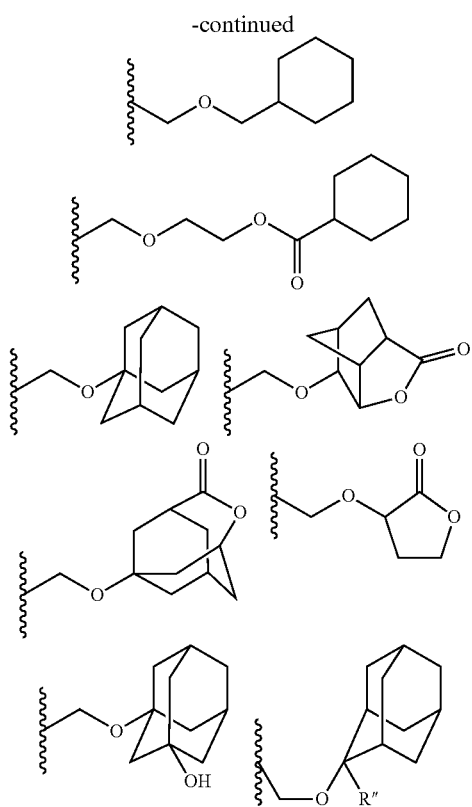

wherein R″ is an alkyl group of 1 to 4 carbon atoms.

2. The resist composition according to claim 1, wherein the compound represented by the formula (1) is a compound represented by the following formula (1-1), and the compound represented by the formula (2) is a compound represented by the following formula (2-1):

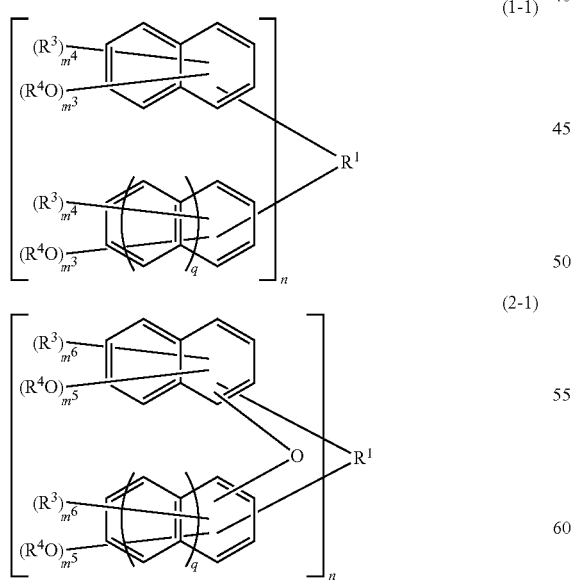

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^3$ is independently a hydrogen atom, a linear, branched, or cyclic alkyl group of 1 to 10 carbon atoms, an aryl group of 6 to 10 carbon atoms, or an alkenyl group of 2 to 10 carbon atoms and may be the same as or different from each other on the same naphthalene ring or benzene ring; each $R^4$ is independently a hydrogen atom or an acid dissociation group; at least one of $R^4$ is an acid dissociation group; structural formulas of repeating units in the formulas (1-1) and (2-1) may be the same as or different from each other; n is an integer of 1 to 4; in the formula (1-1), each $m^3$ is independently an integer of 1 to 7, each $m^4$ is independently an integer of 0 to 6, and each $m^3+m^4$ is independently an integer of 1 to 7; and in the formula (2-1), each $m^5$ is independently an integer of 1 to 6, each $m^6$ is independently an integer of 0 to 5, each $m^5+m^6$ is independently an integer of 1 to 6, and each q is 1 wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group, and wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

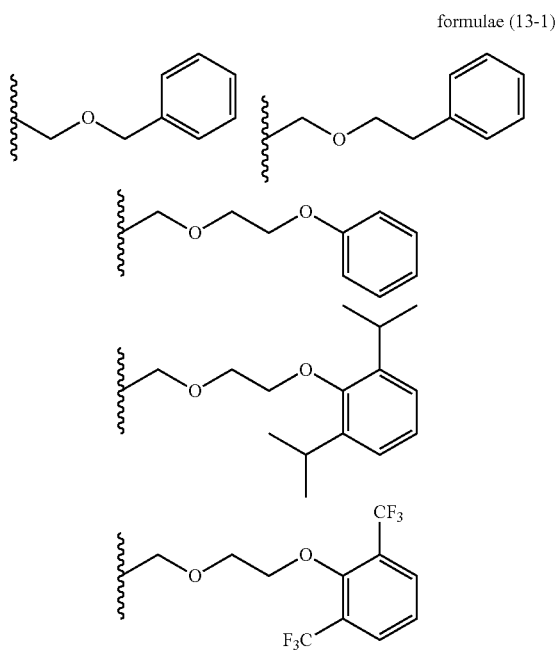

-continued

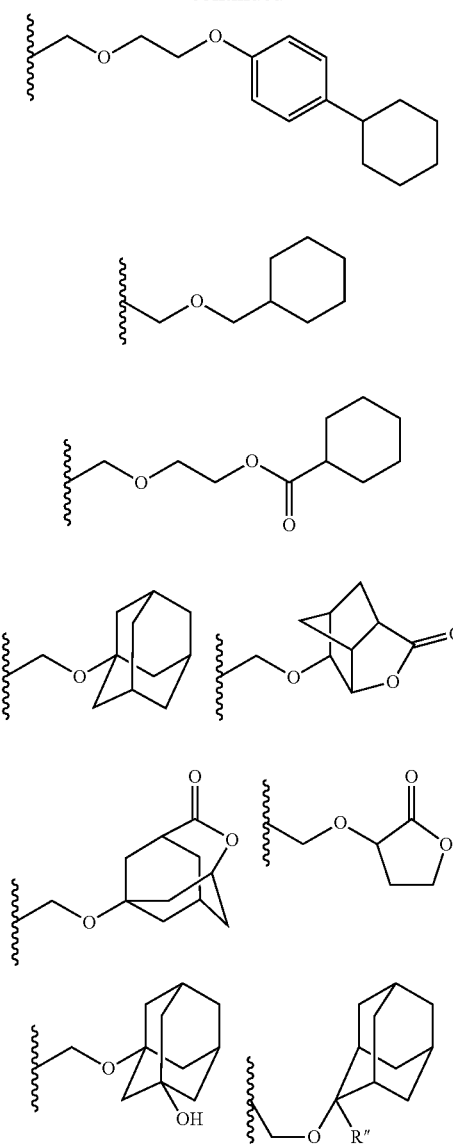

wherein R″ is an alkyl group of 1 to 4 carbon atoms.

3. The resist composition according to claim 1, wherein the compound represented by the formula (1) is a compound represented by the following formula (1-2), and the compound represented by the formula (2) is a compound represented by the following formula (2-2):

(1-2)

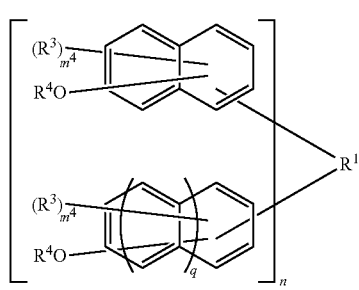

-continued (2-2)

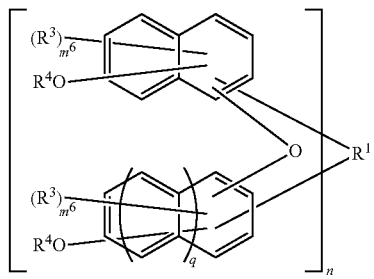

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^3$ is independently a hydrogen atom, a linear, branched, or cyclic alkyl group of 1 to 10 carbon atoms, an aryl group of 6 to 10 carbon atoms, or an alkenyl group of 2 to 10 carbon atoms and may be the same as or different from each other on the same naphthalene ring or benzene ring; each $R^4$ is independently a hydrogen atom or an acid dissociation group; at least one of $R^4$ is an acid dissociation group; structural formulas of repeating units in the formulas (1-2) and (2-2) may be the same as or different from each other; n is an integer of 1 to 4; in the formula (1-2), each $m^4$ is independently an integer of 0 to 6; and in the formula (2-2), each $m^6$ is independently an integer of 0 to 5, and each q is 1 wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group, and wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

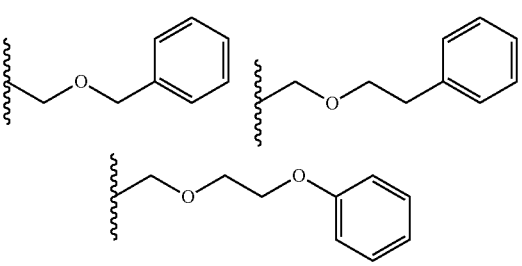

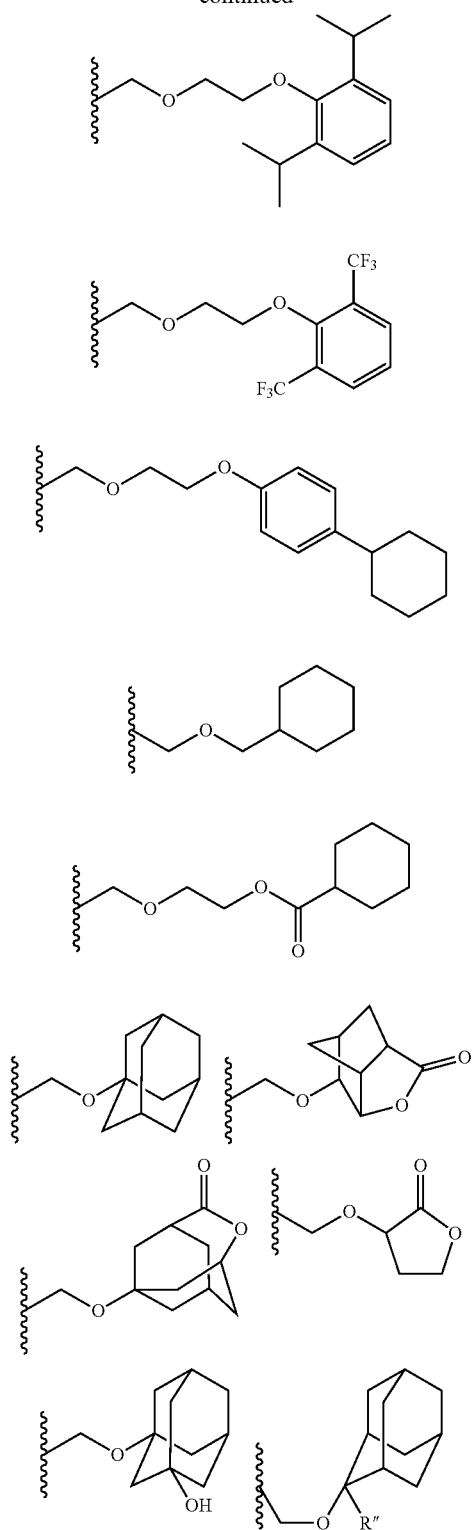

wherein R″ is an alkyl group of 1 to 4 carbon atoms.

4. The resist composition according to claim 1, wherein the compound represented by the formula (1) is a compound represented by the following formula (3), and the compound represented by the formula (2) is a compound represented by the following formula (4):

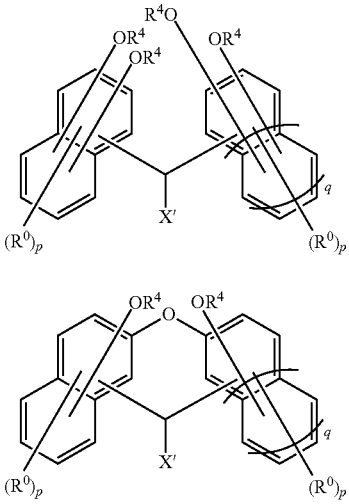

(3)

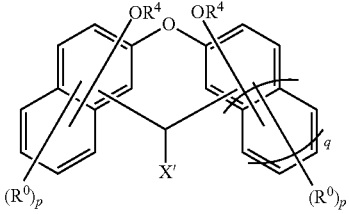

(4)

wherein X′ is a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; each $R^4$ is independently a hydrogen atom or an acid dissociation group; at least one of $R^4$ is an acid dissociation group; each p is independently an integer of 0 to 5; and q is 1 wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group, and wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

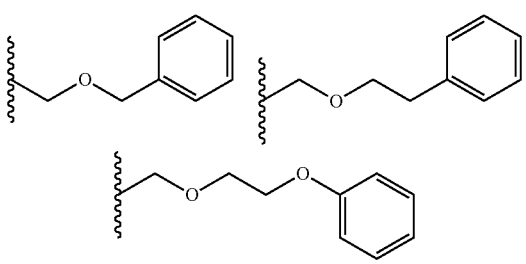

-continued

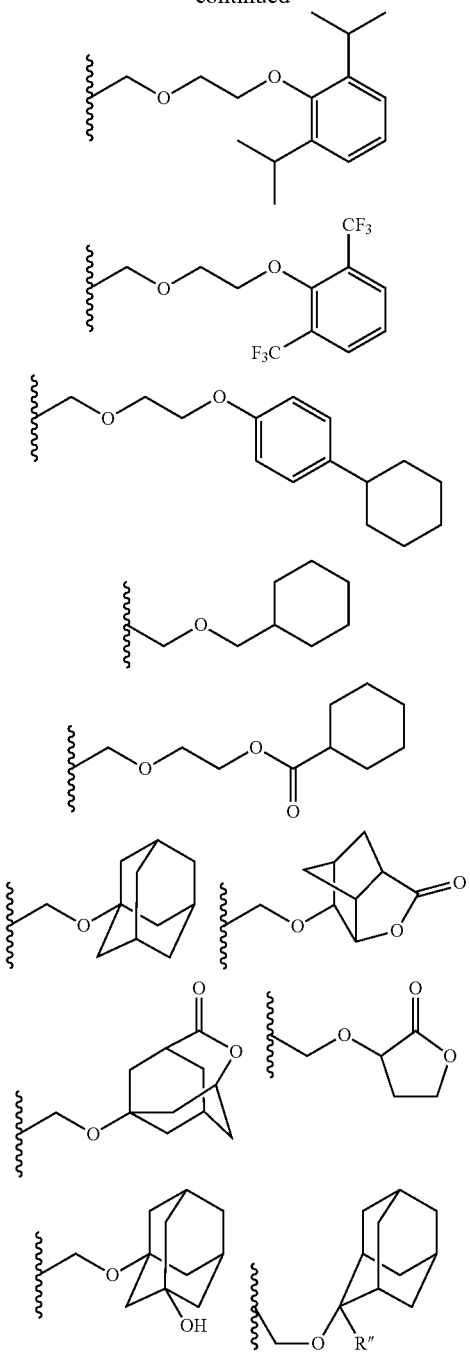

wherein R″ is an alkyl group of 1 to 4 carbon atoms.

5. The resist composition according to claim 1, further comprising a solvent.

6. The resist composition according to claim 1, further comprising an acid diffusion controlling agent.

7. A method for forming a resist pattern, comprising the steps of:
coating a substrate with the resist composition according to claim 1, thereby forming a resist film;
exposing the formed resist film; and
developing the exposed resist film.

8. A polyphenol derivative represented by the following formula (3) or (4):

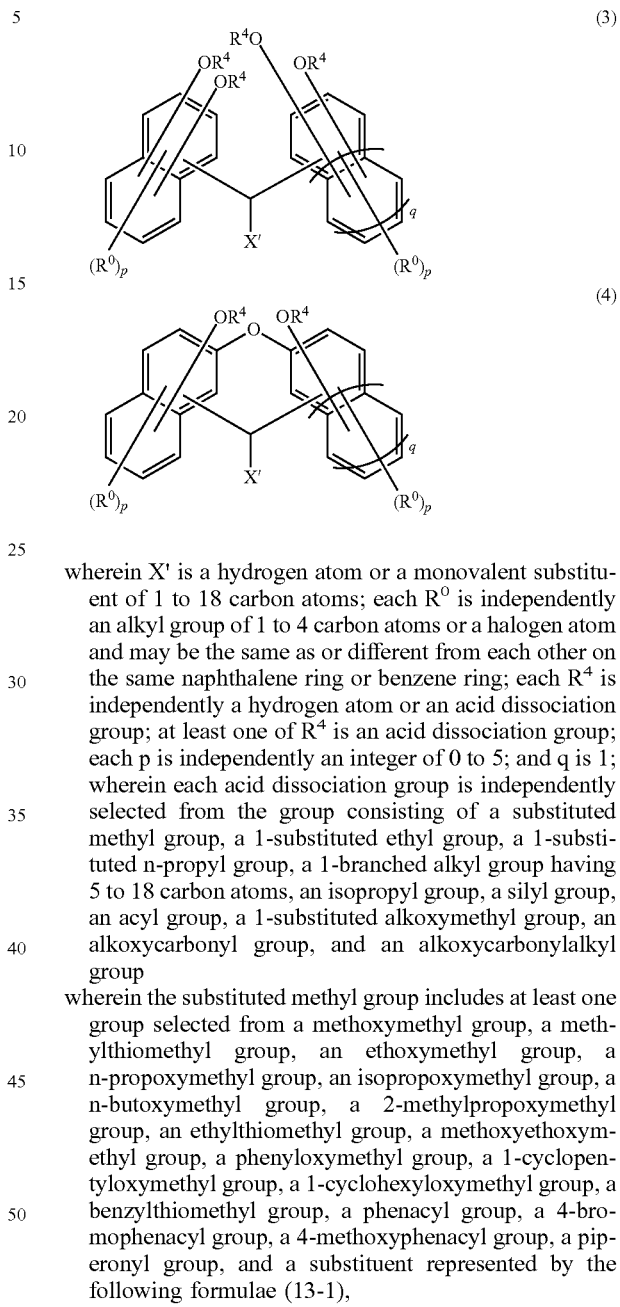

wherein X' is a hydrogen atom or a monovalent substituent of 1 to 18 carbon atoms; each $R^0$ is independently an alkyl group of 1 to 4 carbon atoms or a halogen atom and may be the same as or different from each other on the same naphthalene ring or benzene ring; each $R^4$ is independently a hydrogen atom or an acid dissociation group; at least one of $R^4$ is an acid dissociation group; each p is independently an integer of 0 to 5; and q is 1; wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

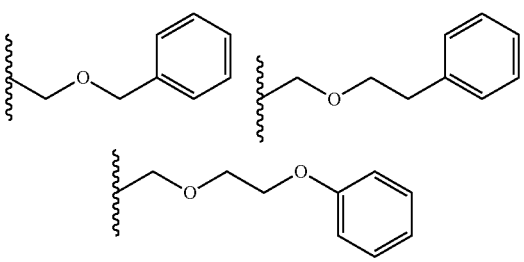

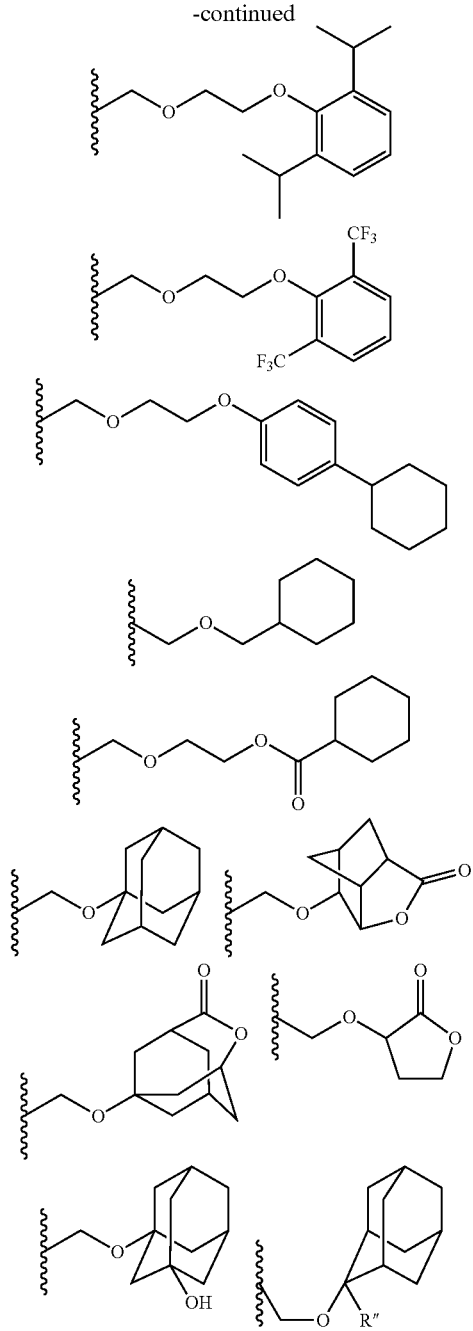

wherein R″ is an alkyl group of 1 to 4 carbon atoms.

9. The resist composition according to claim 2, further comprising a solvent.

10. The resist composition according to claim 3, further comprising a solvent.

11. The resist composition according to claim 4, further comprising a solvent.

12. The resist composition according to claim 2, further comprising an acid diffusion controlling agent.

13. The resist composition according to claim 3, further comprising an acid diffusion controlling agent.

14. The resist composition according to claim 4, further comprising an acid diffusion controlling agent.

15. A method for forming a resist pattern, comprising the steps of:
coating a substrate with the resist composition according to claim 2, thereby forming a resist film;
exposing the formed resist film; and
developing the exposed resist film.

16. A method for forming a resist pattern, comprising the steps of:
coating a substrate with the resist composition according to claim 3, thereby forming a resist film;
exposing the formed resist film; and
developing the exposed resist film.

17. A polyphenol derivative comprising:
a compound represented by the following formula (1) or (2):

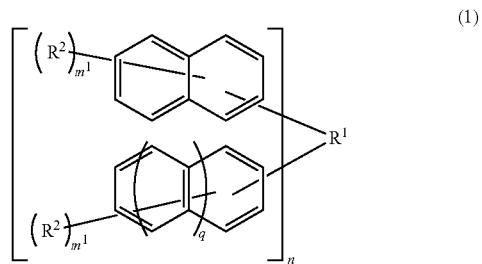

(1)

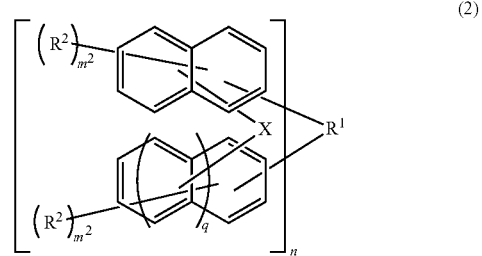

(2)

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^2$ is independently a hydrogen atom, a halogen atom, a linear, branched, or cyclic alkyl group of 1 to 10 carbon atoms, an aryl group of 6 to 10 carbon atoms, an alkenyl group of 2 to 10 carbon atoms, a hydroxyl group, or a group in which a hydrogen atom of a hydroxyl group is substituted with an acid dissociation group, and may be the same as or different from each other on the same naphthalene ring or benzene ring; at least one of $R^2$ is a group in which a hydrogen atom of a hydroxyl group is substituted with an acid dissociation group; n is an integer of 1 to 4; structural formulas of repeating units in the formulas (1) and (2) may be the same as or different from each other; in the formula (1), each $m^1$ is independently an integer of 1 to 7; and in the formula (2), each X is independently an oxygen atom or a sulfur atom, each $m^2$ is independently an integer of 1 to 6, and each q is 1; wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

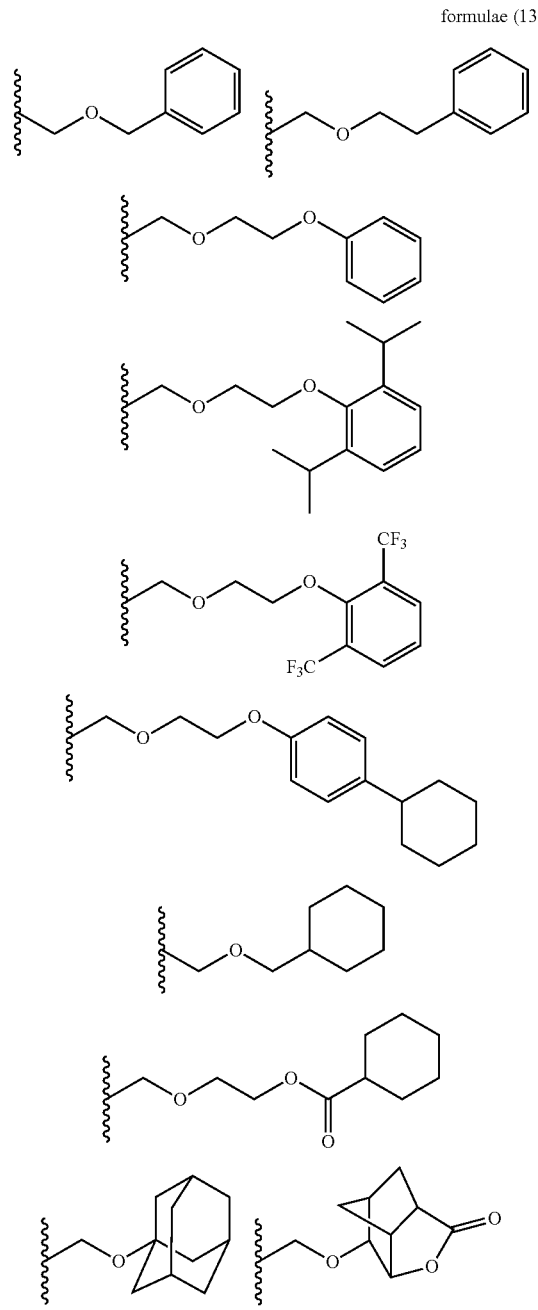

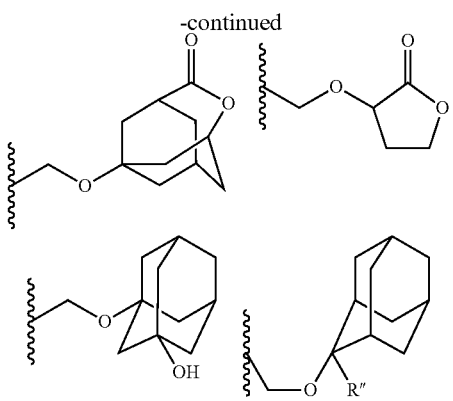

-continued wherein R" is an alkyl group of 1 to 4 carbon atoms.

18. A polyphenol derivative comprising:
a compound represented by the following formula (1-1) or (2-1):

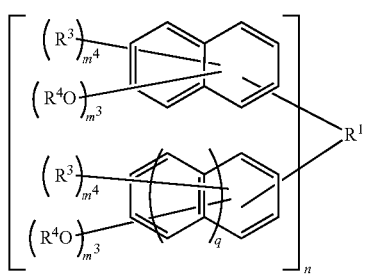

(1-1)

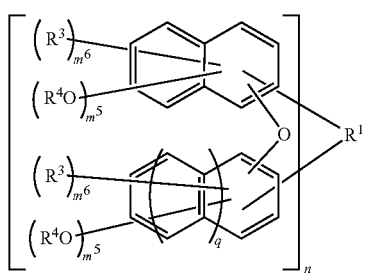

(2-1)

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^3$ is independently a hydrogen atom, a linear, branched, or cyclic alkyl group of 1 to 10 carbon atoms, an aryl group of 6 to 10 carbon atoms, or an alkenyl group of 2 to 10 carbon atoms and may be the same as or different from each other on the same naphthalene ring or benzene ring; each $R^4$ is independently a hydrogen atom or an acid dissociation group; at least one of $R^4$ is an acid dissociation group; structural formulas of repeating units in the formulas (1-1) and (2-1) may be the same as or different from each other; n is an integer of 1 to 4; in the formula (1-1), each $m^3$ is independently an integer of 1 to 7, each $m^4$ is independently an integer of 0 to 6, and each $m^3+m^4$ is independently an integer of 1 to 7; and in the formula (2-1), each $m^5$ is independently an integer of 1 to 6, each $m^6$ is independently an integer of 0 to 5, each $m^5+m^6$ is independently an integer of 1 to 6, and each q is 1; wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

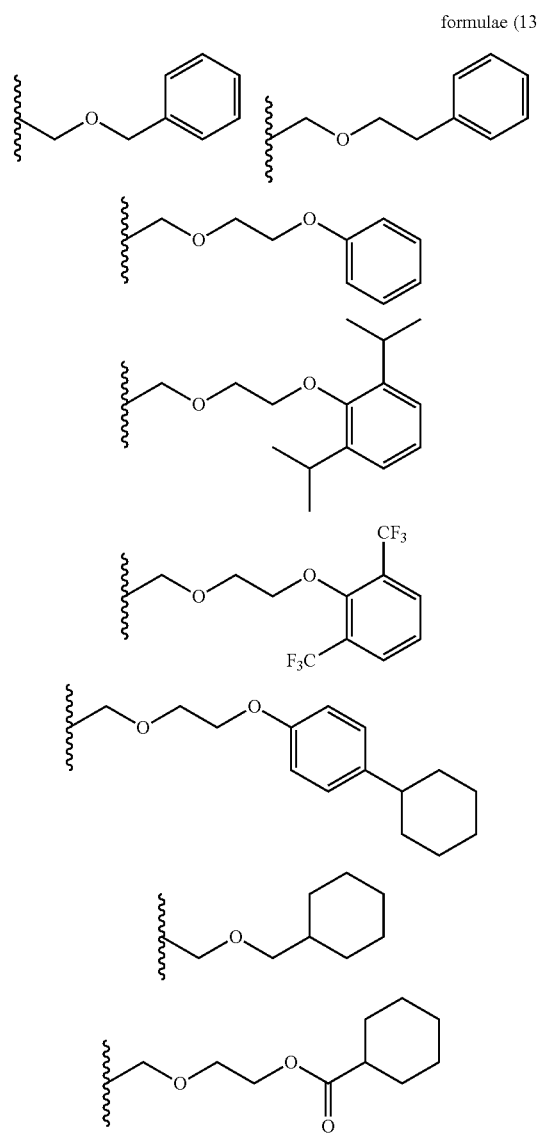

-continued

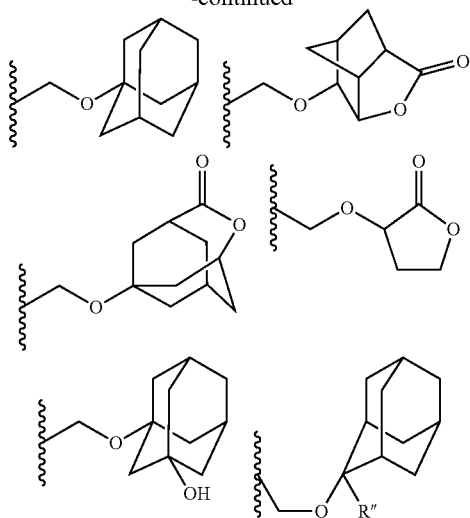

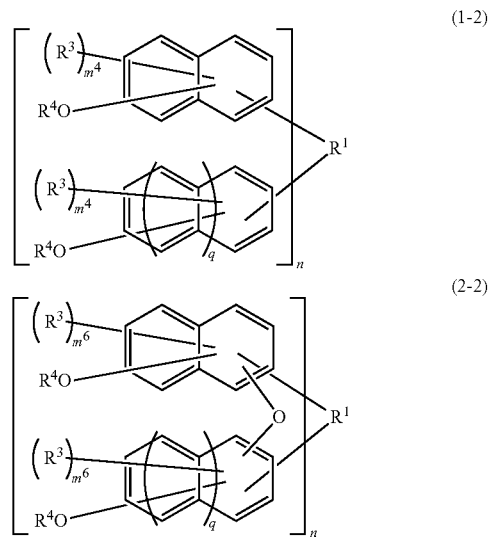

wherein R" is an alkyl group of 1 to 4 carbon atoms.

19. A polyphenol derivative comprising:
a compound represented by the following formula (1-2) or (2-2):

(1-2)

(2-2)

wherein $R^1$ is a single bond or a 2n-valent hydrocarbon group of 1 to 30 carbon atoms wherein the hydrocarbon group may have a cyclic hydrocarbon group (except for an aromatic group), a double bond, a heteroatom, or an aromatic group of 6 to 30 carbon atoms; each $R^3$ is independently a hydrogen atom, a linear, branched, or cyclic alkyl group of 1 to 10 carbon atoms, an aryl group of 6 to 10 carbon atoms, or an alkenyl group of 2 to 10 carbon atoms and may be the same as or different from each other on the same naphthalene ring or benzene ring; each $R^4$ is independently a hydrogen atom or an acid dissociation group; at least one of $R^4$ is an acid dissociation group; structural formulas of repeating units in the formulas (1-2) and (2-2) may be the same as or different from each other; n is an integer of 1 to 4; in the formula (1-2), each $m^4$ is independently an integer of 0 to 6; and in the formula (2-2), each $m^6$ is independently an integer of 0 to 5, and each q is 1; wherein each acid dissociation group is independently selected from the group consisting of a substituted methyl group, a 1-substituted ethyl group, a 1-substituted n-propyl group, a 1-branched alkyl group having 5 to 18 carbon atoms, an isopropyl group, a silyl group, an acyl group, a 1-substituted alkoxymethyl group, an alkoxycarbonyl group, and an alkoxycarbonylalkyl group
wherein the substituted methyl group includes at least one group selected from a methoxymethyl group, a methylthiomethyl group, an ethoxymethyl group, a n-propoxymethyl group, an isopropoxymethyl group, a n-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1), formulae (13-1)

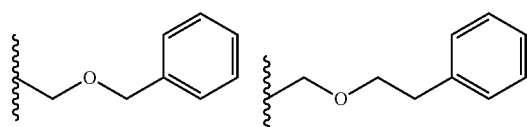

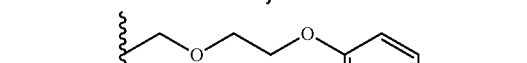

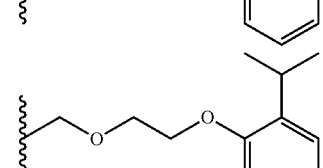

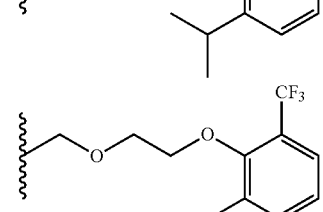

-continued

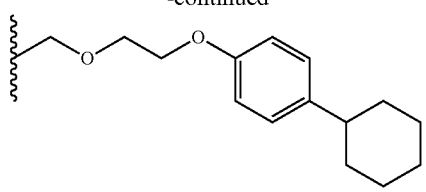

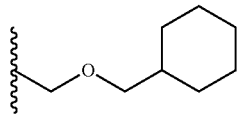

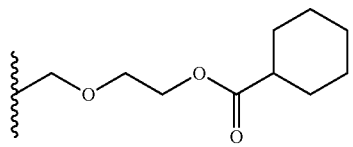

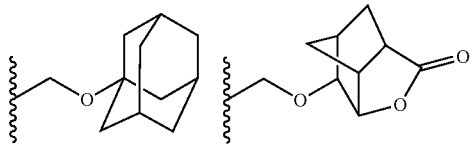

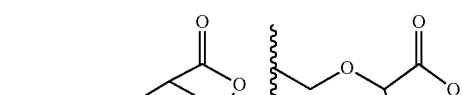

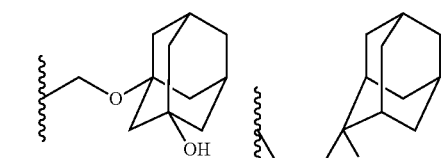

wherein R″ is an alkyl group of 1 to 4 carbon atoms.

* * * * *

UNITED STATES PATENT AND TRADEMARK OFFICE
CERTIFICATE OF CORRECTION

PATENT NO. : 10,377,734 B2  
APPLICATION NO. : 14/766658  
DATED : August 13, 2019  
INVENTOR(S) : Masatoshi Echigo and Masako Yamakawa Page 1 of 1

It is certified that error appears in the above-identified patent and that said Letters Patent is hereby corrected as shown below:

On the Title Page

Item (56) References Cited, under Other Publications, please delete "JP2012" and insert -- JP2014 --, therefor.

In the Claims

Column 65, Line (43-55):

In Claim 1, delete " 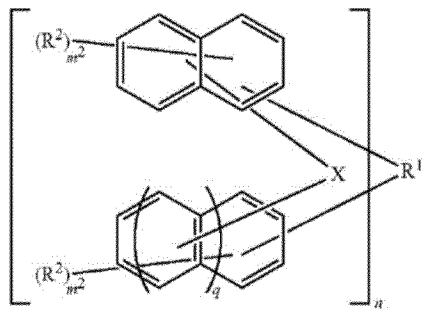 " and insert

-- 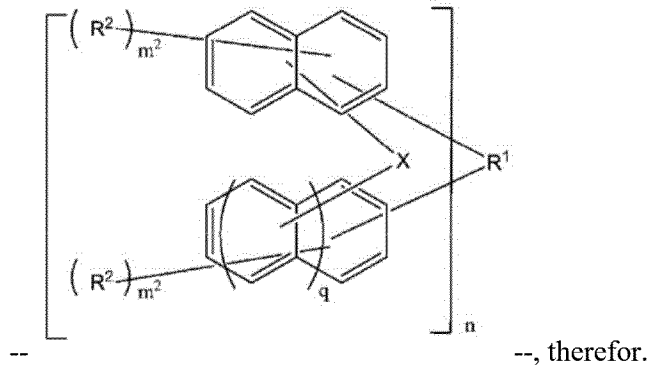 --, therefor.

Signed and Sealed this  
Seventeenth Day of December, 2019

Andrei Iancu  
*Director of the United States Patent and Trademark Office*